US009428492B2

(12) United States Patent
Kuduk et al.

(10) Patent No.: US 9,428,492 B2
(45) Date of Patent: *Aug. 30, 2016

(54) SECONDARY ALCOHOL SUBSTITUTED TRIAZOLES AS PDE10 INHIBITORS

(71) Applicant: Merck Sharp & Dohme Corp., Rahway, NJ (US)

(72) Inventors: Scott D. Kuduk, Harleysville, PA (US); Christopher D. Cox, Harleysville, PA (US); Vadim Y. Dudkin, Chalfont, PA (US); Carol A. McVean, Lansdale, PA (US); Thomas S. Reger, Lansdale, PA (US); Justin T. Steen, Perkasie, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/442,838

(22) PCT Filed: Nov. 11, 2013

(86) PCT No.: PCT/US2013/069380
§ 371 (c)(1),
(2) Date: May 14, 2015

(87) PCT Pub. No.: WO2014/078220
PCT Pub. Date: May 22, 2014

(65) Prior Publication Data
US 2015/0284368 A1    Oct. 8, 2015

Related U.S. Application Data

(60) Provisional application No. 61/726,655, filed on Nov. 15, 2012.

(51) Int. Cl.
*C07D 403/14*   (2006.01)
*A61K 31/506*   (2006.01)
*A61K 31/4184*  (2006.01)
*A61K 31/4196*  (2006.01)

(52) U.S. Cl.
CPC ......... *C07D 403/14* (2013.01); *A61K 31/4184* (2013.01); *A61K 31/4196* (2013.01); *A61K 31/506* (2013.01)

(58) Field of Classification Search
CPC ........... C07D 403/14; A61K 31/4196; A61K 31/4184; A61K 31/506
USPC .................................. 544/324, 328; 514/256
See application file for complete search history.

(56) References Cited

U.S. PATENT DOCUMENTS

2003/0229110 A1   12/2003   Adams et al.
2009/0176829 A1   7/2009    Verhoest et al.
2011/0306590 A1   12/2011   Allen et al.

FOREIGN PATENT DOCUMENTS

| WO | WO2012044561 | 4/2012 |
| WO | WO2012054366 | 4/2012 |
| WO | WO2012147890 | 11/2012 |
| WO | WO2013028590 | 2/2013 |
| WO | WO2013052395 | 4/2013 |
| WO | WO2013052526 | 4/2013 |
| WO | WO2013074390 | 5/2013 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Jordan, Nature Reviews: Drug Discovery, vol. 2, Issue 3, pp. 205-213 (2003).*
Becker et al., Phosphodiesterase Inhibitors-Are They Potential Neuroleptic Drugs?, Behavioural Brain research, 2008, pp. 155-160, 186.
Fujishige et al., Cloning and Characterization of a Novel Human Phosphodiesterase that Hydrolyzes Both cAMP and cGMP (PDE10A), J. Bilogical Chemical, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Obach et al., Mechanism-Based Inactivation of Human Cytochrome P450, Drug Metabolism and Disposition, 2007, pp. 246-255, 35.
Schmidt et al., Pre-clincal Characterization of Selective PHosphodiesterease 10A Inhibitors: A New Therapeutic Approach to the Treatment of Schizophrenia, J. of Pharmacology and Experimental Thereapeutics, 2008, pp. 690-690, 325.
Siuciak et al., Inhibiton of the Striatum-Enriched Phosphodiesterease PDE10A: A novel Approach to the Treament of Psychosis, Neuropharmacology, 2006, pp. 386-396, 51.

(Continued)

*Primary Examiner* — Deepak Rao
(74) *Attorney, Agent, or Firm* — Sylvia A. Ayler; John C. Todaro

(57) ABSTRACT

The present invention is directed to secondary alcohol substituted triazole compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

16 Claims, No Drawings

(56) References Cited

OTHER PUBLICATIONS

Soderling et al., Isolation and Characterization of a Dual-Substrate Phosphodiesterase Gene Family: PDE10A, Proc. Natl. Acad. Sci. USA, Jun. 1999, pp. 7071-7076, 96.

Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.

* cited by examiner

SECONDARY ALCOHOL SUBSTITUTED TRIAZOLES AS PDE10 INHIBITORS

CROSS REFERENCE TO RELATED APPLICATIONS

This application is the National Stage of International Application No. PCT/US2013/069380 filed on Nov. 11, 2013, which claims the benefit under 35 U.S.C. 119(e) of U.S. Provisional Application No. 61/726,655, filed Nov. 15, 2012.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers may be responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP may also be responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., J. Biol. Chem. (1999) 274:18438-18445; Loughney et al., Gene (1999) 234: 109-117; Soderling et al., PNAS, USA (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., Expert Opin. Ther. Patents (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions. For additional background information on PDE10 compounds see U.S. Ser. Nos. 61/544,055 and 61/544,065, both filed Oct. 6, 2011; WO2012/044561 and PCT application number PCT/US12/051522, filed Aug. 20, 2012.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A may be desirable as therapeutics for neurological and psychiatric disorders.

SUMMARY OF THE INVENTION

The present invention is directed to secondary alcohol substituted triazole compounds which may be useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

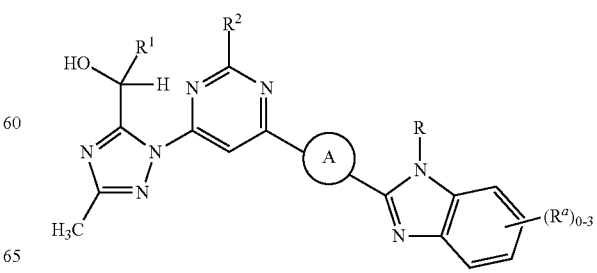

I wherein:
A represents

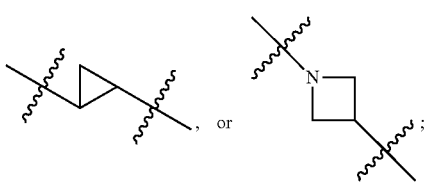 [SMILES: *C1CC1* ; *C1CN(*)C1], or ;

R represents H or $C_{1-6}$alkyl;
$R^1$ is selected from the groups consisting of $(CH_2)_nC_{1-4}$ haloalkyl, $C_{1-6}$alkyl, $C_{3-6}$cycloalkyl, $C_{6-10}$ wary, said alkyl cycloalkyl, and aryl is unsubstituted or substituted with 1 to 3 groups of $R^a$;
$R^2$ is selected from the group consisting of H, O—R, CN, $O(CH_2)_nOR$, $OCHR(CH_2)_nOR$, SR, $SO_2R$, S(O)R, $N(R)_2$, $C(O)N(R)_2$, $C_{1-3}$ haloalkyl, $O(CH_2)_nC_{1-3}$haloalkyl, $O(CH_2)_nC_{3-6}$cycloalkyl, $(CH_2)_nC_{5-10}$heterocycle, $C_{1-6}$alkyl, and $C_{3-10}$cycloalkyl, said alkyl, cycloalkyl, and heterocycle is unsubstituted or substituted with 1 to 3 groups of $R^a$;
$R^a$ is selected from the group consisting of:
(1) halogen,
(2) hydroxyl,
(3) $C_{1-6}$alkyl,
(4) —$(CH_2)_nO$—R,
(5) $(CH_2)_n C_{6-10}$aryl,
(6) $(CH_2)_nC_{5-10}$ heterocycle,
(7) $OC_{1-5}$ haloalkyl;
(8) $CO_2R$;
(9) $C(O)N(R)_2$;
(10) $(CH_2)_nC(O)R$;
(11) CN,
(12) $(CH_2)_nN(R)_2$;
(13) $(CH_2)_nC_{3-6}$cycloalkyl,
(14) $(CH_2)_nC_{1-3}$ haloalkyl;
n represents 0-4,
or a pharmaceutically acceptable salt thereof.

An embodiment of the present invention includes compounds wherein A is

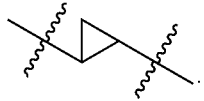 [SMILES: *C1CC1*].

An embodiment of the present invention includes compounds wherein A is

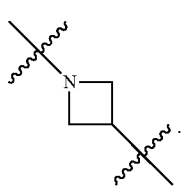 [SMILES: *C1CN(*)C1].

An embodiment of the present invention includes compounds wherein $R^1$ is $(CH_2)_nC_{1-4}$haloalkyl or $C_{1-6}$alkyl.
An embodiment of the present invention includes compounds wherein $R^1$ is $C_{1-6}$ alkyl. A subembodiment of this invention is realized when $R^1$ is methyl, ethyl or propyl. Another subembodiment of this invention is realized when $R^1$ is methyl.

An embodiment of the present invention includes compounds wherein $R^1$ is $(CH_2)_nC_{1-4}$ haloalkyl. A subembodiment of this invention is realized when $R^1$ is $CF_3$.

An embodiment of the present invention includes compounds wherein $R^1$ is optionally substituted $C_{6-10}$ aryl. A subembodiment of this invention is realized when $R^1$ is optionally substituted phenyl.

An embodiment of the present invention includes compounds wherein $R^1$ is $C_{3-6}$ cycloalkyl. A subembodiment of this invention is realized when $R^1$ is cyclopropyl, cyclobutyl, or cyclohexyl. A further subembodiment of this invention is realized when $R^1$ is cyclohexyl.

Another embodiment of the present invention includes compounds wherein $R^2$ is selected from the group consisting of O—R, CN, $C_{1-3}$ haloalkyl, $C_{1-6}$alkyl, and $C_{3-10}$cycloalkyl, said alkyl and cycloalkyl is unsubstituted or substituted with 1 to 3 groups of $R^a$. A subembodiment of this invention is realized when $R^2$ is methyl, ethyl, propyl, $CF_3$, cyclopropyl. Another subembodiment of this invention is realized when $R^2$ is methyl. Another subembodiment of this invention is realized when $R^2$ is $CF_3$. Another subembodiment of this invention is realized when $R^2$ is cyclopropyl.

Another embodiment of the present invention includes compounds wherein $R^1$ is $(CH_2)_nC_{1-3}$haloalkyl, $C_{1-6}$alkyl, or $C_{3-6}$cycloalkyl, and $R^2$ is selected from the group consisting of O—R, CN, $C_{1-3}$ haloalkyl, $C_{1-6}$alkyl, and $C_{3-10}$cycloalkyl, said alkyl unsubstituted or substituted with 1 to 3 groups of $R^a$.

Another embodiment of the present invention includes compounds wherein R is methyl, $R^1$ is methyl, ethyl, propyl, $CF_3$, or cyclohexyl and $R^2$ is methyl, ethyl, propyl, $CF_3$, or cyclopropyl An embodiment of the present invention includes compounds represented by structural formula Ia:

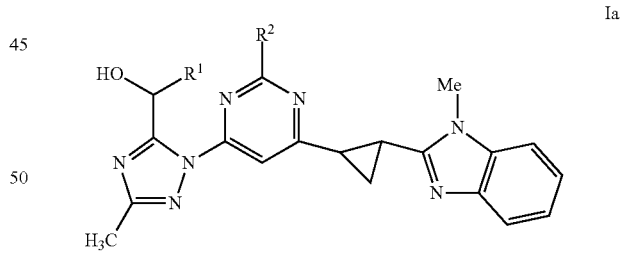

Ia wherein $R^1$, and $R^2$ are as originally described. A subembodiment of the invention of formula Ia is realized when $R^1$ is methyl, ethyl, propyl, $CF_3$, phenyl, or cyclohexyl. A subembodiment of formula Ia is realized when $R^1$ is methyl, ethyl, or propyl. Another subembodiment of the invention of formula Ia is realized when $R^2$ is methyl, ethyl, propyl, $CF_3$, or cyclopropyl. A subembodiment of formula Ia is realized when $R^1$ is methyl, ethyl, or propyl and $R^2$ is methyl, $CF_3$, or cyclopropyl. A subembodiment of formula Ia is realized when $R^1$ is methyl, and $R^2$ is methyl, or $CF_3$.

An embodiment of the present invention includes compounds represented by structural formula Iaa:

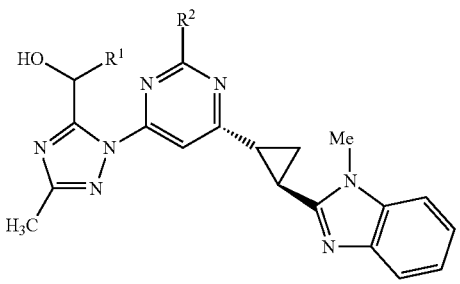

wherein R¹, and R² are as originally described. A subembodiment of the invention of formula Iaa is realized when R¹ is methyl, ethyl, propyl, CF₃, phenyl, or cyclohexyl. A subembodiment of formula Iaa is realized when R¹ is methyl, ethyl, or propyl. Another subembodiment of the invention of formula Iaa is realized when R² is methyl, ethyl, propyl, CF₃, or cyclopropyl. A subembodiment of formula Iaa is realized when R¹ is methyl, ethyl, or propyl and R² is methyl, CF₃, or cyclopropyl. A subembodiment of formula Iaa is realized when R¹ is methyl, and R² is methyl, or CF₃.

An embodiment of the present invention of formula I includes compounds represented by structural formula Ib:

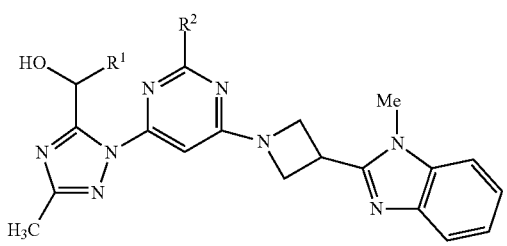

wherein R¹, and R² are as originally described. A subembodiment of the invention of formula Ib is realized when R¹ is methyl, ethyl, propyl, CF₃, phenyl, or cyclohexyl. A subembodiment of formula Ib is realized when R¹ is methyl, ethyl, or propyl. Another subembodiment of the invention of formula Ib is realized when R² is methyl, ethyl, propyl, CF₃, or cyclopropyl. A subembodiment of formula Ib is realized when R¹ is methyl, ethyl, or propyl and R² is methyl, CF₃, or cyclopropyl. A subembodiment of formula Ib is realized when R¹ is methyl, and R² is methyl, or CF₃.

Examples of compounds of this invention include:

1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
(S)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
(R)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
1-(3-methyl-1-(6-(3-(1-methyl-1H-benzo[d]imidazol-2-yl)azetidin-1-yl)-2-(trifluoromethyl)pyrimidin-4-yl)-1H-1,2,4-triazol-5-yl)ethanol;
1-(1-(2-methoxy-6-(3-(1-methyl-1H-benzo[d]imidazol-2-yl)azetidin-1-yl)pyrimidin-4-yl)-3-methyl-1H-1,2,4-triazol-5-yl)ethanol;
1-(1-(2-cyclopropyl-6-(3-(1-methyl-1H-benzo[d]imidazol-2-yl)azetidin-1-yl)pyrimidin-4-yl)-3-methyl-1H-1,2,4-triazol-5-yl)ethanol;
2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
(S)-2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
(R)-2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
2,2-difluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
2-fluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;
(S)-cyclohexyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;
(R)-cyclohexyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;
(S)-(3-methyl-1-(2-methyl-6-(3-(1-methyl-1H-benzo[d]imidazol-2-yl)azetidin-1-yl)pyrimidin-4-yl)-1H-1,2,4-triazol-5-yl)(phenyl)methanol;
(R)-(3-methyl-1-(2-methyl-6-(3-(1-methyl-1H-benzo[d]imidazol-2-yl)azetidin-1-yl)pyrimidin-4-yl)-1H-1,2,4-triazol-5-yl)(phenyl)methanol;
1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;
2-methyl-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;
cyclopropyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;
3,3,3-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;
1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;
(R)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;
(S)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;
(R)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol;
(S)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol;
2,2,2-trifluoro-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;
1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol;
2-methyl-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol;

1-(3-methyl-1-(6-((1R,2R)-2-(1-methyl-1H-benzo[d]imida-
zol-2-yl)cyclopropyl)-2-(trifluoromethyl)pyrimidin-4-
yl)-1H-1,2,4-triazol-5-yl)ethanol;

(S)-1-(3-methyl-1-(6-((1R,2R)-2-(1-methyl-1H-benzo[d]
imidazol-2-yl)cyclopropyl)-2-(trifluoromethyl)pyrimi-
din-4-yl)-1H-1,2,4-triazol-5-yl)ethanol;

1-(1-(2-cyclopropyl-6-((1R,2R)-2-(1-methyl-1H-benzo[d]
imidazol-2-yl)cyclopropyl)pyrimidin-4-yl)-3-methyl-1H-
1,2,4-triazol-5-yl)ethanol (S)-1-(1-(2-cyclopropyl-6-((1R,2R)-2-(1-methyl-1H-benzo
[d]imidazol-2-yl)cyclopropyl)pyrimidin-4-yl)-3-methyl-
1H-1,2,4-triazol-5-yl)ethanol;

or pharmaceutically acceptable salts thereof.

Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "haloalkyl" refers to an alkyl substituent as described herein containing at least one halogen substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" or "O-alkyl" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3, 4-dichlorophenyl, 3-chloro-4-fluoro-phenyl, 2,4 fluor-3-propylphenyl. As another non-limiting example, substituted n-octyls include 2, 4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:
  (a) halo, cyano, oxo, carboxy, formyl, nitro, amino, amidino, guanidino, and
  (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfinyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" or "halo" refer to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

Compounds described herein may contain one or more double bonds and may thus give rise to cis/trans isomers as well as other conformational isomers. The present invention includes all such possible isomers as well as mixtures of such isomers unless specifically stated otherwise.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of generic Formula I, Ia, Iaa, and Ib the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE10 dysfunction in a patient such as a mammal in need of such inhibition comprising the administration of an effective amount of the compound. In addition to primates, especially humans, a variety of other mammals may be treated according to the method of the present invention. The subject compounds may be useful in a method of inhibiting PDE10 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals may be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, may provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum may result in increased cAMP/cGMP signaling and striatal output, which has the potential to restore behavioral inhibition that is impaired in cognitive disease such as schizophrenia. Regulation and integration of glutamatergic and dopaminergic inputs may enhance cognitive behavior, while suppressing or reducing unwanted behavior. Thus, in one embodiment compounds of the invention provide a possible method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "'selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention may provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention may provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention may provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention may provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention may provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention may provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention may provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention may provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., J. Biomol Screen, 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to phosphodiesterase assays (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. Neuropharmacology (2006) 51:386-396; Becker, et al. Behav Brain Res (2008) 186(2): 155-60; Threlfell, et al., J Pharmacol Exp Ther (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. J Pharmacol Exp Ther (2008) 325:681-690; Threlfell, et al., J Pharmacol Exp Ther (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product # R7506), at a final concentration of 50 nM are made in the assay buffer (10 mM Tris HCl, pH 7.2, 10 mM MgCl$_2$, 0.05% NaN$_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

$$\text{Polarization } (mP) = 1000 * (S/So - P/Po)/(S/So + P/Po).$$

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=> same as this control), the minimum inhibition at the high plateau relative to the "0% Inhibition Control" (Imin, e.g. 0=> same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \, mP - 100\% \, mP)(I\max - I\min)}{1 + \left[\frac{[\text{Drug}]}{\left(10^{-pK_I}\left(1 + \frac{[\text{Substrate}]}{K_M}\right)\right)}\right]^{nH}} +$$

$$100\% \, mP + (0\% \, mP - 100\% \, mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL, and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL, of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE10 enzyme in the aforementioned assays, generally with a Ki of less than about 1 µM. Many of compounds within the present invention had activity in inhibiting the human PDE10 enzyme in the aforementioned assays, generally with a Ki of less than about 0.1 µM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 µM, preferably less than or about 0.1 µM. The present invention also includes compounds within the generic scope of the invention which possess activity as inhibitors of other phosphodiesterase enzymes.

The subject compounds may be further useful in a method for the prevention, treatment, control, amelioration, or reduction of risk of the diseases, disorders and conditions noted herein. The subject compounds may be further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5-HT_{1A}$ agonists or antagonists, especially $5-HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds may be further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: h: hour; Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DCM: dichloromethane; DMA-DMA: N,N-dimethylacetamide dimethyl acetal; DME: 1,2-dimethoxyethane; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

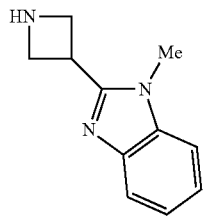

Scheme:

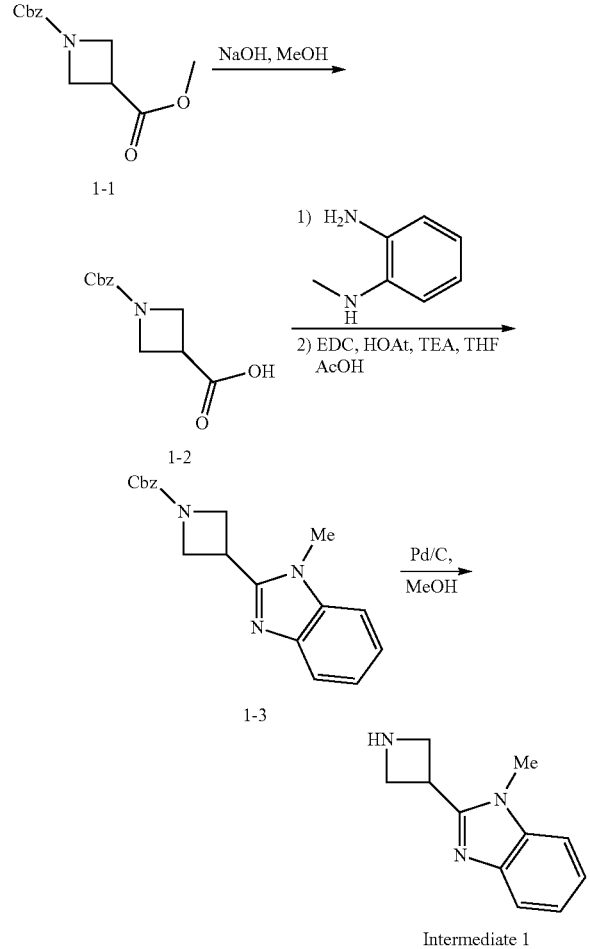

Step 1:

1-[(benzyloxy)carbonyl]azetidine-3-carboxylic acid (1-2)

1-1 (4.5 g, 18.05 mmol) was dissolved in MeOH (90 mL) and 2 M NaOH (27 mL, 54.2 mmol) was added. After stirring at room temperature for 3 h, the solution was concentrated to ~20 mL. 1 M HCl was added to the resulting solution until pH reached 4 and the solution was extracted with EtOAc (2×). The combined organic layer was dried over $Na_2SO_4$, filtered, and concentrated to provide 1-2 as a white solid. MS: m/z=236.2 (M+H).

Step 2:

benzyl 3-(1-methyl-1H-benzimidazol-2-yl)azetidine-1-carboxylate (1-3)

1-2 (3.0 g, 12.75 mmol) was dissolved in THF (64 mL) and N-methylbenzene-1,2-diamine (2.02 g, 16.58 mmol), EDC (2.93 g, 15.30 mmol), HOAt (2.08 g, 15.30 mmol), and Hunig's base (6.7 mL, 38.3 mmol) were added. After stirring for 18 h at room temperature, the reaction solution was concentrated. The residue was then dissolved in acetic acid (30 mL), stirred at room temperature for 2 h, the solvent was concentrated under reduced pressure. The residue was partitioned between ethyl acetate and 5% aqueous $NaHCO_3$. The organic layer was dried over $Na_2SO_4$, filtered, and concentrated. The crude residue was purified by silica gel chromatography (EtOAc/Hexanes) to provide 1-3 as an off-white solid. MS: m/z=322.4 (M+H).

Step 3:

2-(azetidin-3-yl)-1-methyl-1H-benzimidazole (Intermediate 1)

A solution of 1-3 (3.32 g, 10.33 mmol) in MeOH (52 mL) was subjected to 2 cycles of the evacuation/backfilling with nitrogen and then treated with 10% Pd/C (1.1 g). The evacuation/backfilling with nitrogen procedure was repeated two times and then the nitrogen atmosphere was exchanged for a hydrogen atmosphere by evacuation/backfilling with a balloon of hydrogen. After stirring for 3 h under hydrogen at room temperature, the reaction mixture was filtered through celite, and washed with additional MeOH (20 mL). The filtrate was concentrated to yield Intermediate 1 as brown solid. MS: m/z=188.2 (M+H).

Intermediate 2

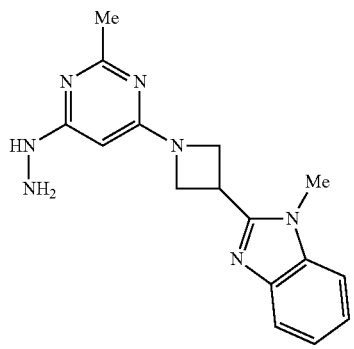 [SMILES: Cc1nc(NN)cc(N2CC(c3nc4ccccc4n3C)C2)n1]

Scheme:

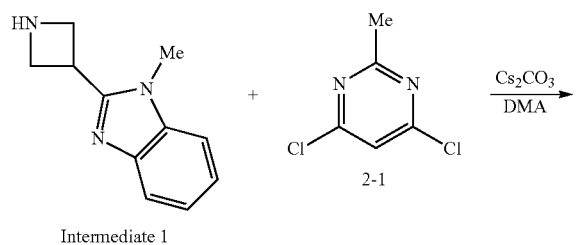

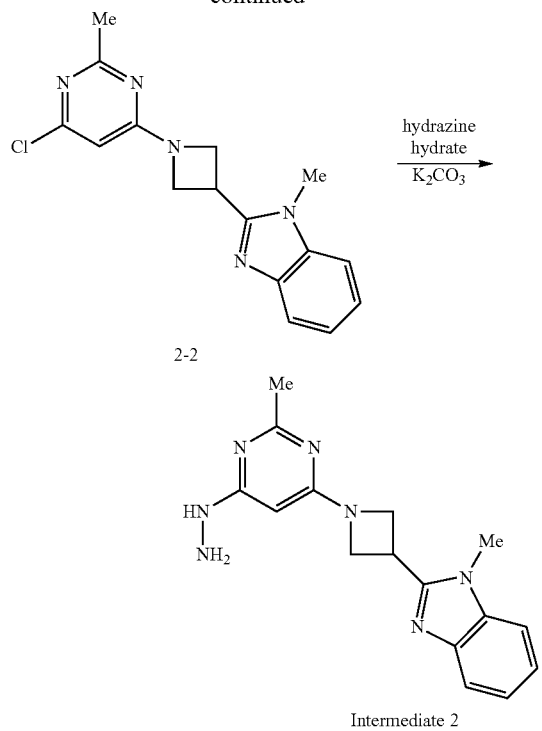

Step 1:

2-(1-(6-chloro-2-methylpyrimidin-4-yl)azetidin-3-yl)-1-methyl-1H-benzo[d]imidazole (2-2)

Intermediate 1 (8.2 g, 43.8 mmol), 2-1 (8.2 g, 50.4 mmol) and $Cs_2CO_3$ (21.4 g, 65.7 mmol) were suspended in DMA (100 mL) and the mixture was stirred at 50° C. for 3 h. The mixture was cooled to rt, diluted with EtOAc (200 mL), and washed sequentially with water, brine, and water (150 mL each). The combined aqueous phase was back extracted with EtOAc (2×100 mL). The combined organic layer was dried over $MgSO_4$, filtered, and concentrated to give a brownish solid. The solid was triturated with a diethyl ether/DCM mixture (95/5) and then filtered and dried under vacuum to give 2-2 as a light brown solid. MS: m/z=314.2 (M+H).

Step 2:

2-(1-(6-hydrazinyl-2-methylpyrimidin-4-yl)azetidin-3-yl)-1-methyl-1H-benzo[d]imidazole (Intermediate 2)

Compound 2-2 (900 mg, 2.87 mmol), hydrazine hydrate (431 mg, 8.6 mmol) and $K_2CO_3$ (1.2 g, 8.6 mmol) were suspended in 2-MeTHF (8 mL) in a vial that was capped and heated at 85° C. for 16 h. After cooling to room temperature, the reaction was filtered and the collected solids were washed with water and ether and dried over suction to give Intermediate 2 as a white solid. MS: m/z=310.3 (M+H).

The following intermediates were prepared in a similar manner by substituting the appropriate starting material:

| Intermediate | Structure |
|---|---|
| 3 | 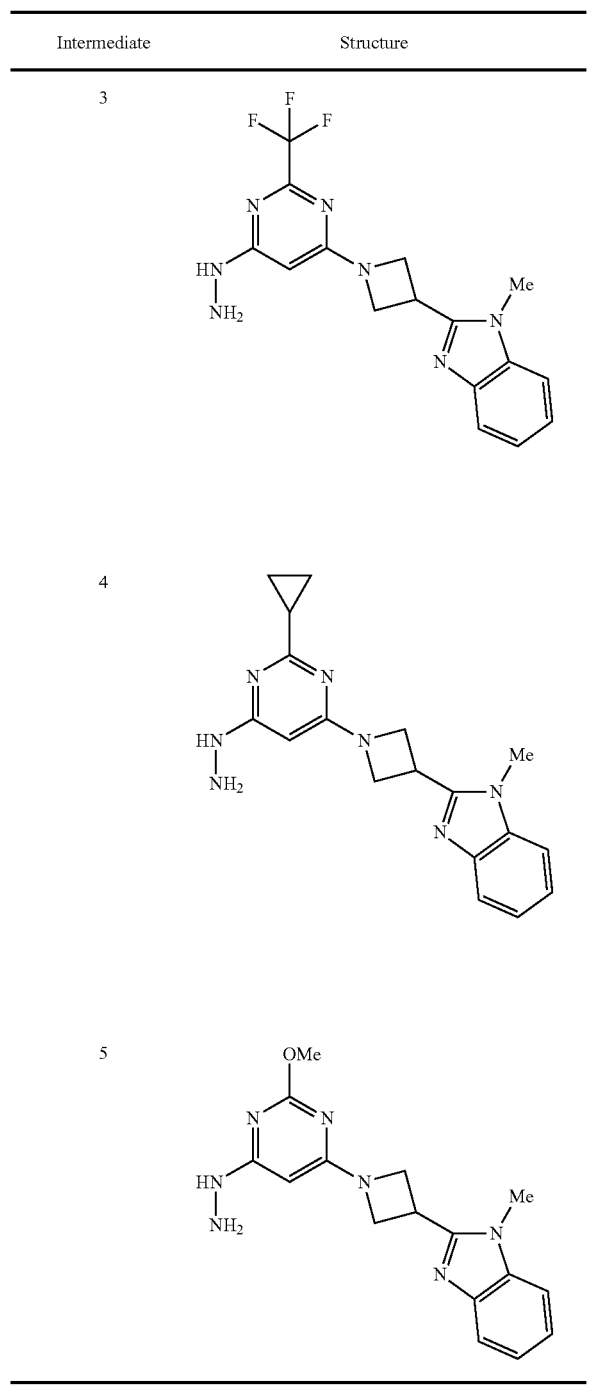 |
| 4 | 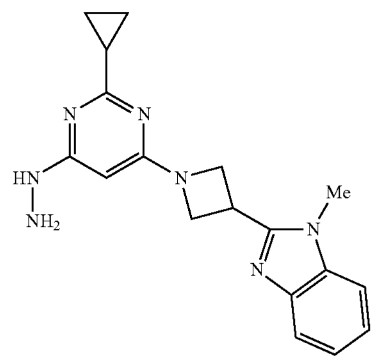 [SMILES: Cn1c(C2CN(c3cc(NN)nc(C4CC4)n3)C2)nc2ccccc21] |
| 5 | 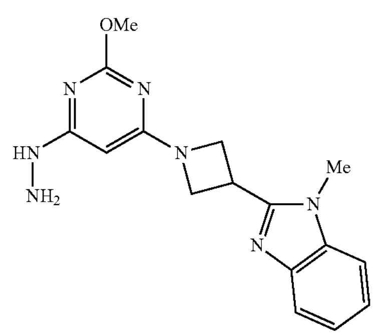 [SMILES: COc1nc(NN)cc(N2CC(c3nc4ccccc4n3C)C2)n1] |

Intermediate 6

Scheme:

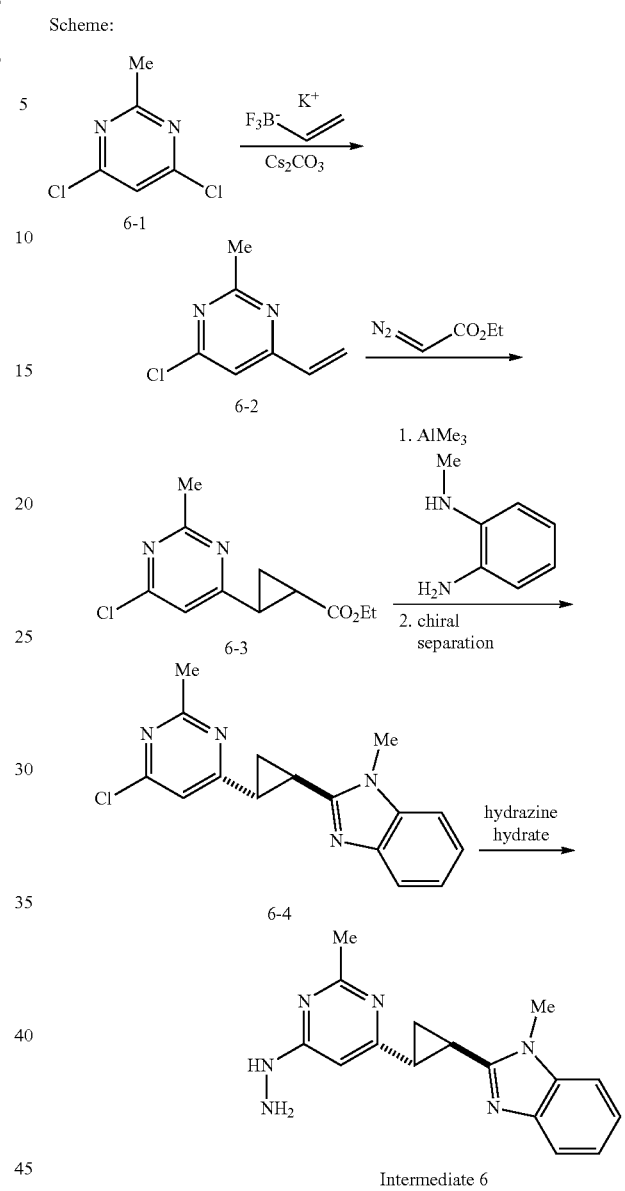

Step 1:

4-chloro-2-methyl-6-vinylpyrimidine (6-2)

A reaction vessel containing 6-1 (26.3 g, 161 mmol), potassium trifluoro(vinyl)borate (20 g, 149 mmol), cesium carbonate (97 g, 299 mmol) and butyldi-1-adamantylphosphine (2.89 g, 8.06 mmol) was evacuated and backfilled with nitrogen (3×). Toluene (452 ml) and water (45 mL) were added and the reaction was purged with nitrogen for 20 min. Finally, palladium acetate (0.905 g, 4.03 mmol) was added, the mixture was purged with nitrogen for 10 min, and then heated at 100° C. for 2 h. The mixture was cooled to room temperature, diluted with EtOAc (200 mL), washed with water (2×200 mL), dried, filtered and concentrated under reduced pressure. The residue was purified by silica gel chromatography (0-100% EtOAc/hexanes) to give 6-2 as a white solid. MS: m/z=155.1 (M+H).

Step 2:

ethyl 2-(6-chloro-2-methylpyrimidin-4-yl)cyclopropanecarboxylate (6-3)

To a solution of 6-2 (15.0 g, 97 mmol) in toluene (300 mL) heating at 100° C. under a nitrogen atmosphere was added a solution of ethyl diazoacetate (30.2 mL, 291 mmol) in toluene (100 mL) over 1.5 h. Heating was continued for 2 h after which the reaction mixture was cooled to room temperature and concentrated to dryness. The residue was partitioned between saturated sodium bicarbonate solution (1 L) and ethyl acetate (1 L). The organic layer was separated, dried over sodium sulfate, filtered and concentrated under reduced pressure. The crude residue was purified by silica gel chromatography (0-100% EtOAc/hexanes) to give 6-3 (trans isomer) as a colorless oil. MS: m/z=241.1 (M+H).

Step 3:

2-((1R,2R)-2-(6-chloro-2-methylpyrimidin-4-yl) cyclopropyl)-1-methyl-1H-benzo[d]imidazole (6-4)

To a solution of N1-methylbenzene-1,2-diamine (5.08 g, 41.5 mmol) in toluene (100 mL) was added a 2M solution of trimethylaluminum (22.85 ml, 45.7 mmol) in toluene dropwise over 2 h with periodic cooling in an ice bath to prevent an exotherm. After addition was complete, the resulting dark brown mixture was warmed to room temperature and stirred for 15 min. The mixture was re-cooled in an ice bath and a solution of 6-3 (5 g, 20.8 mmol) in toluene (20 mL) was added drop-wise over 2 h, after which the reaction was warmed to room temperature. After stirring for 18 h, the reaction was cooled in an ice bath and slowly quenched with water. The mixture was filtered through a pad of celite washing with ethyl acetate. The filtrate was repeatedly washed with saturated copper (II) sulfate solution until a yellow orange organic layer was obtained and no N1-methylbenzene-1,2-diamine was observed by LCMS. The organic layer was dried over magnesium sulfate, filtered and concentrated in vacuo to give the crude product which was purified by silica gel chromatography (0-100% EtOAc/hexanes) to afford racemic 6-4. The racemic compound was further purified by preparative chiral SFC on a ChiralCel OJ-H column (3 cm id×25 cm length) eluting with 70% carbon dioxide/30% methanol with 0.1% triethylamine modifier in isocratic mode at 80 mL/min. The first eluting peak was identified as the desired R,R enantiomer (6-4) and was used in subsequent steps. $^1$H NMR (400 MHz, CDCl$_3$) δ 7.71-7.66 (m, 1H), 7.31-7.23 (m, 3H), 7.19 (s, 1H), 3.83 (s, 3H), 2.86-2.79 (m, 2H), 2.67 (s, 3H), 1.96 (m, 2H); MS: m/z=299.2 (M+H).

Step 4:

2-((1R,2R)-2-(6-hydrazinyl-2-methylpyrimidin-4-yl) cyclopropyl)-1-methyl-1H-benzo[d]imidazole (Intermediate 6)

A slurry of 6-4 (4 g, 13.39 mmol), hydrazine hydrate (1.261 ml, 40.2 mmol) and potassium carbonate (5.55 g, 40.2 mmol) in 2-MeTHF (100 ml) was heated at 80° C. for 16 h. After cooling to room temperature, the reaction mixture was partitioned between water and ethyl acetate. The organic layer was separated, dried over sodium sulfate, filtered and concentrated to afford Intermediate 6 as a tan solid. MS: m/z=295.4 (M+H).

The following intermediates were prepared in a similar manner by substituting the appropriate starting materials:

| Intermediate | Structure |
|---|---|
| 7 | (pyrimidine with CF$_3$ at 2-position, HN-NH$_2$ at 4-position, cyclopropyl linker to 1-methyl-1H-benzo[d]imidazole) |
| 8 | (pyrimidine with cyclopropyl at 2-position, HN-NH$_2$ at 4-position, cyclopropyl linker to 1-methyl-1H-benzo[d]imidazole) |
| 9 | (pyrimidine with OMe at 2-position, HN-NH$_2$ at 4-position, cyclopropyl linker to 1-methyl-1H-benzo[d]imidazole) |

Intermediate 10

(3,3-difluoro-2-((tert-butyldimethylsilyl)oxy)propanamide)

Scheme:

10-1 (F$_2$CH-CH(OH)-CH(OEt)) → [KCN, KH$_2$PO$_4$] → 10-2 (F$_2$CH-CH(OH)-CH(OH)CN) → [HCl] → 10-3 (F$_2$CH-CH(OH)-C(O)NH$_2$) → [TBDMS—Cl, TEA] → Intermediate 10 (F$_2$CH-CH(OTBDMS)-C(O)NH$_2$)

Step 1:

3,3-difluoro-2-hydroxypropanenitrile (10-2)

To a solution of 1-ethoxy-2,2-difluoroethanol (10-1) (2.0 g, 16 mmol) in water (16 mL) was added potassium cyanide (1.0 g, 16 mmol) followed by potassium dihydrogen phosphate (2.2 g, 16 mmol). The mixture was stirred at room temperature for 90 min then poured into saturated aqueous sodium carbonate (50 mL) and extracted with ethyl acetate (3×50 mL). The combined organic layer was dried over sodium sulfate, filtered and concentrated in vacuo to afford 10-2 as a yellow oil that was used without further purification.

Step 2:

3,3-difluoro-2-hydroxypropanamide (10-3)

A solution of 10-2 (600 mg, 5.6 mmol) in conc HCl (6.90 mL, 84.0 mmol) was stirred at room temperature for 16 h. The mixture was concentrated in vacuo and azeotroped with toluene (2×) to provide 10-3 that was used without further purification. $^1$H NMR (400 MHz, d$_6$-DMSO) δ 7.48 (br s, 1H), 7.36-7.10 (m, 2H), 6.34-5.97 (m, 1H), 4.34-4.09 (m, 1H).

Step 3:

2-((tert-butyldimethylsilyl)oxy)-3,3-difluoropropanamide (Intermediate 10)

To a solution of 3,3-difluoro-2-hydroxypropanamide (700 mg, 5.6 mmol) in DMF (5.6 mL) was added tert-butyldimethylchlorosilane (1.10 g, 7.28 mmol) and triethylamine (1.17 mL, 8.40 mmol). The mixture was stirred at room temperature for 3 h, diluted with ethyl acetate and washed with saturated aqueous sodium bicarbonate (2×) and brine. The organic layer was dried over sodium sulfate, filtered, and concentrated to provide Intermediate 10 that was used without further purification. MS: m/z=240.3 (M+H).

Intermediate 11

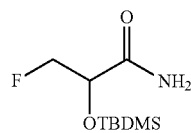

Scheme:

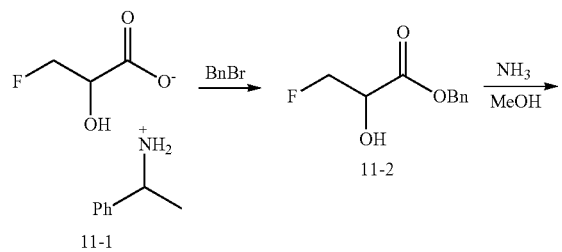

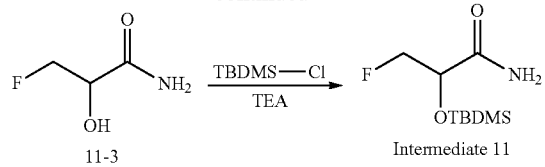

Step 1:

benzyl 3-fluoro-2-hydroxypropanoate (11-2)

To a solution of 1-phenylethanaminium 3-fluoro-2-hydroxypropanoate (11-1) (0.14 g, 0.61 mmol) in DMF (1 mL) was added benzyl bromide (0.087 mL, 0.73 mmol). The mixture was stirred at room temperature overnight, diluted with EtOAc, washed with water and brine, dried over sodium sulfate, filtered, and concentrated. The residue was purified by silica gel chromatography (0-50% EtOAc/hexanes) to provide 11-2. HRMS: 198.0688 found, 198.0692 required (M+).

Step 2:

3-fluoro-2-hydroxypropanamide (11-3)

A solution of 11-2 (0.20 g, 1.01 mmol) in 7M ammonia/MeOH (2.88 mL, 20.2 mmol) was heated at 70° C. in a sealed vial overnight. The mixture was concentrated in vacuo to provide crude 11-3 that was used without further purification.

Step 3:

2-((tert-butyldimethylsilyl)oxy)-3-fluoropropanamide (Intermediate 11)

To a crude solution of 11-3 (0.050 g, 0.47 mmol) in DMF (0.5 mL) was added tert-butyldimethylchlorosilane (0.091 g, 0.61 mmol) and triethylamine (0.098 mL, 0.70 mmol). The mixture was stirred at room temperature for 1 h then diluted with EtOAc. The mixture was washed with saturated aqueous sodium bicarbonate (2×) and brine. The organic layer was dried over sodium sulfate, filtered, and concentrated, providing crude Intermediate 11 that was used without further purification. MS: m/z=222.3 (M+H).

Intermediate 12

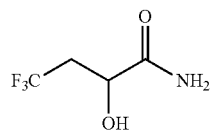

Scheme:

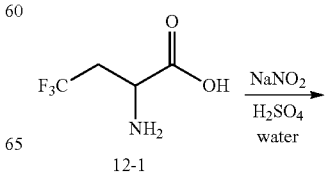

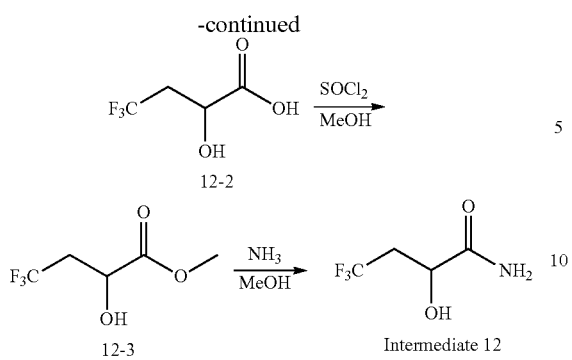

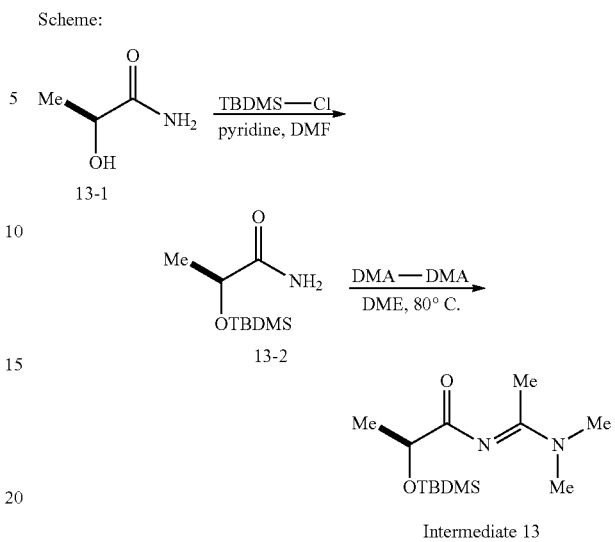

Step 1:

4,4,4-trifluoro-2-hydroxybutanoic acid (12-2)

A solution of 2-amino-4,4,4-trifluorobutanoic acid (12-1) (1 g, 6.37 mmol) in 1 N aqueous sulfuric acid (10.00 ml, 10 mmol) was cooled to 0° C. To the cooled reaction mixture was added a solution of sodium nitrite (1.1 g, 15.9 mmol) in water (5 mL) dropwise over 40 minutes via addition funnel. The reaction mixture was then warmed to room temperature and stirred for 16 h. Sodium chloride was added to the reaction until complete saturation was achieved. The resulting aqueous mixture was washed with ethyl acetate (3×50 mL) and the combined organic layer was dried over sodium sulfate, filtered and concentrated to dryness to afford 12-2 as a white crystalline solid. $^1$H NMR (500 MHz, DMSO-$d_6$) δ 2.51 (m, 1H), 2.67 (m, 1H), 4.24 (dd, J=8.60, 3.60 Hz, 1H), 5.74 (br s, 1H), 12.89 (br s, 1H).

Step 2:

methyl 4,4,4-trifluoro-2-hydroxybutanoate (12-3)

Thionyl chloride (0.139 ml, 1.90 mmol) was added dropwise to a solution of 12-2 (200 mg, 1.27 mmol) in MeOH (2 ml) at room temperature. After addition was complete, the reaction was heated in a sealed vessel at 70° C. for 2 h. The reaction was cooled to room temperature and concentrated in vacuo. The residue was diluted with 7N NH$_3$/MeOH (3 mL) and filtered to remove insolubles. The filtrate was concentrated to dryness to afford 12-3 as a clear oil.

Step 3:

4,4,4-trifluoro-2-hydroxybutanamide (Intermediate 12)

A solution of 12-3 (200 mg, 1.16 mmol) in 7N NH$_3$/MeOH (10 mL) was heated at 70° C. overnight. The reaction mixture was filtered, and the filtrate was concentrated to dryness. The residue was dissolved in 1,2-dimethoxyethane (10 mL) and filtered to remove insolubles. The filtrate was concentrated to dryness to afford Intermediate 12. $^1$H NMR (500 MHz, DMSO-$d_6$) δ 7.40 (br s, 1H), 7.34 (br s, 1H), 5.93 (m, 1H), 4.10 (m, 1H), 2.64-2.65 (m, 1H), 2.40-2.41 (m, 1H).

Intermediate 13

Step 1:

(S)-2-((tert-butyldimethylsilyl)oxy)propanamide (13-2)

A solution of (S)-2-hydroxypropanamide (13-1) (30 g, 337 mmol) and tert-butyldimethylchlorosilane (66.0 g, 438 mmol) in pyridine (101 ml, 1246 mmol) and DMF (90 ml) was stirred at room temperature for 16 h. The reaction mixture was filtered to remove insolubles and the filtrate was partitioned between saturated aqueous sodium bicarbonate solution (500 mL) and EtOAc (500 mL). The organic layer was washed with saturated aqueous sodium bicarbonate solution (2×100 mL), brine (3×100 mL) and water (3×100 mL). The organic layer was dried over sodium sulfate, filtered and concentrated to afford 13-2 as a viscous yellow oil. MS: m/z=204.0 (M+H).

Step 2:

(S)-2-((tert-butyldimethylsilyl)oxy)-N-(1-(dimethylamino)ethylidene)propanamide (Intermediate 13)

A solution of 13-2 (3.8 g, 18.69 mmol) and 1,1-dimethoxy-N,N-dimethylethanamine (2 g, 15.02 mmol) in 1,2-dimethoxyethane (40 ml) was heated at 80° C. under nitrogen in a sealed tube for 2 h. The resulting reaction mixture containing Intermediate 13 was carried forward without purification or further characterization. MS: m/z=273.4 (M+H).

The following intermediates were prepared in a similar manner to Intermediate 13. The required primary amide starting materials were either commercially available or prepared by routes described for Intermediates 10-12.

| Intermediate | Structure |
|---|---|
| 14 | Me,,,,(C=O)-N=C(Me)-N(Me)Me, OTBDMS |

35
-continued

| Intermediate | Structure |
|---|---|

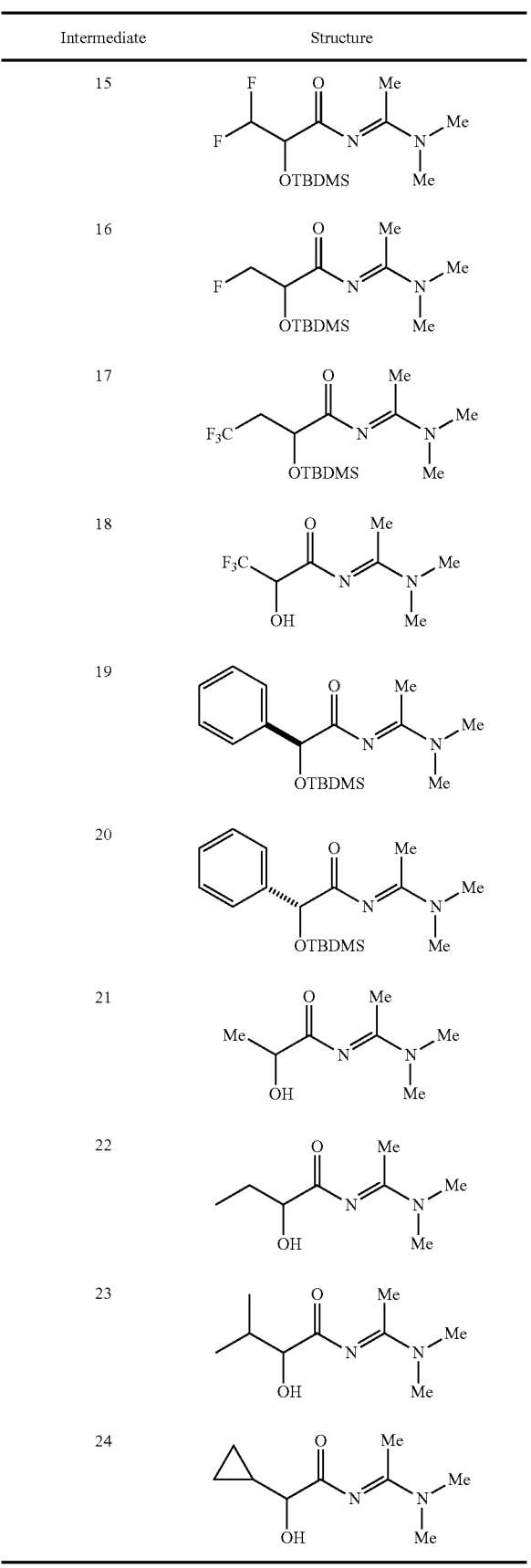

36

Example 1

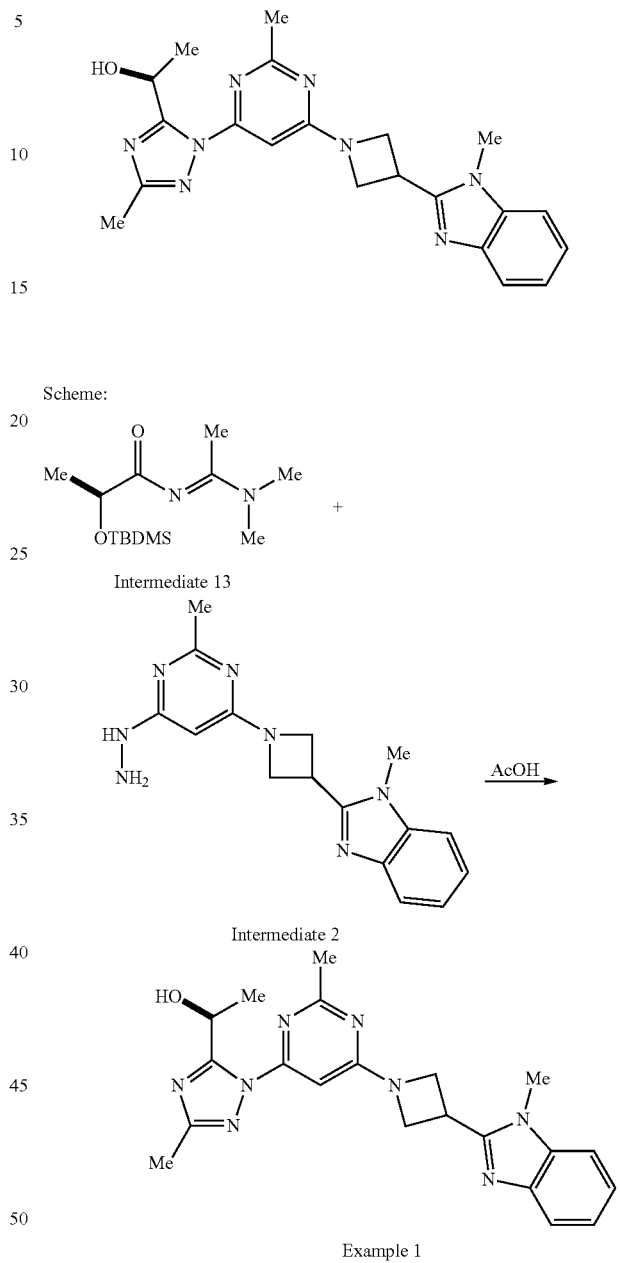

(S)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol (Example 1)

A solution of Intermediate 2 (11.0 g, 35.6 mmol) in AcOH (100 mL) was added to crude Intermediate 13 (24.2 g, 89 mmol, prepared by heating the corresponding primary amide in neat DMA-DMA at 50° C. overnight followed by removal of excess DMA-DMA by rotary evaporation). The reaction mixture was allowed to stir for 10 min at room temperature and then heated at 80° C. for 1 h. Sampling of the reaction by LCMS suggested cyclization to the silyl-protected hydroxy triazole had occurred. The reaction was allowed to stir at 80° C. for an additional 16 h at which point complete de-silylation of the hydroxy group had occurred. The reaction was cooled to room temperature, poured carefully over saturated aqueous sodium bicarbonate solution (200 mL), and the aqueous layer was made basic to pH~8 by the addition of solid sodium bicarbonate. The solution was extracted with ethyl acetate and the organic layer was dried over sodium sulfate, filtered, and concentrated. The crude product was purified by silica gel chromatography (0-10% 2-propanol/DCM) to give Example 1 as a white solid. $^1$H NMR (500 MHz, CDCl$_3$) δ 7.76-7.74 (m, 1H), 7.35-7.28 (m, 3H), 6.96 (m, 1H), 6.62 (s, 1H), 5.12-5.07 (m, 1H), 4.71-4.58 (br s, 4H), 4.34-4.24 (m, 1H), 3.75 (s, 3H), 2.54 (s, 3H), 2.43 (s, 3H) 1.71 (d, J=6.6 Hz, 3H); MS: m/z=405.5 (M+H).

Example 2

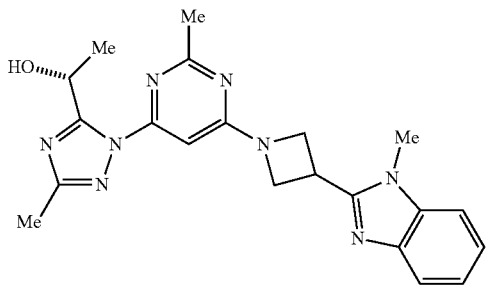 [SMILES: Cc1nc(N2CC(c3nc4ccccc4n3C)C2)cc(-n2nc(C)nc2[C@@H](C)O)n1]

(R)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol (Example 2)

To a solution of Intermediate 2 (1.2 g, 3.9 mmol) in AcOH (35 mL) was added the DME solution of Intermediate 14 (5.1 g, 18.7 mmol). The reaction mixture was allowed to stir for 10 min at room temperature and then heated at 80° C. for 30 min. Sampling of the reaction by LCMS suggested cyclization to the silyl-protected hydroxy triazole had occurred. The DME was removed by rotary evaporation and the remaining mixture was allowed to stir at 80° C. for an additional 16 h at which point complete de-silylation of the hydroxy group had occurred. The reaction was cooled to room temperature, poured carefully over saturated aqueous sodium bicarbonate solution (200 mL), and the aqueous layer was made basic to pH~8 by the addition of solid sodium bicarbonate. The solution was extracted with ethyl acetate (200 mL) and the organic layer was dried over sodium sulfate, filtered, and concentrated. The crude product was purified by silica gel chromatography (0-10% 2-propanol/DCM) to give Example 2 as a white solid. $^1$H NMR (500 MHz, CDCl$_3$) δ 7.77-7.75 (m, 1H), 7.35-7.24 (m, 3H), 6.95 (m, 1H), 6.62 (s, 1H), 5.12-5.07 (m, 1H), 4.68-4.58 (br s, 4H), 4.34-4.28 (m, 1H), 3.75 (s, 3H), 2.54 (s, 3H), 2.43 (s, 3H) 1.71 (d, J=6.6 Hz, 3H); MS: m/z=405.3 (M+H).

Example 3

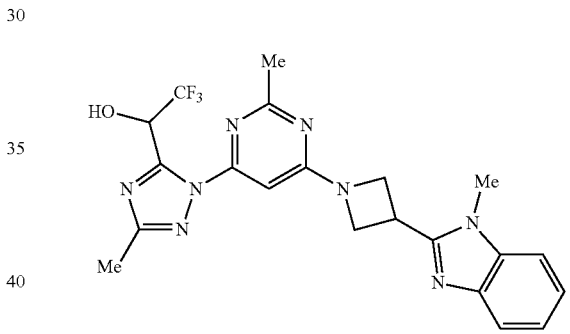

Scheme:

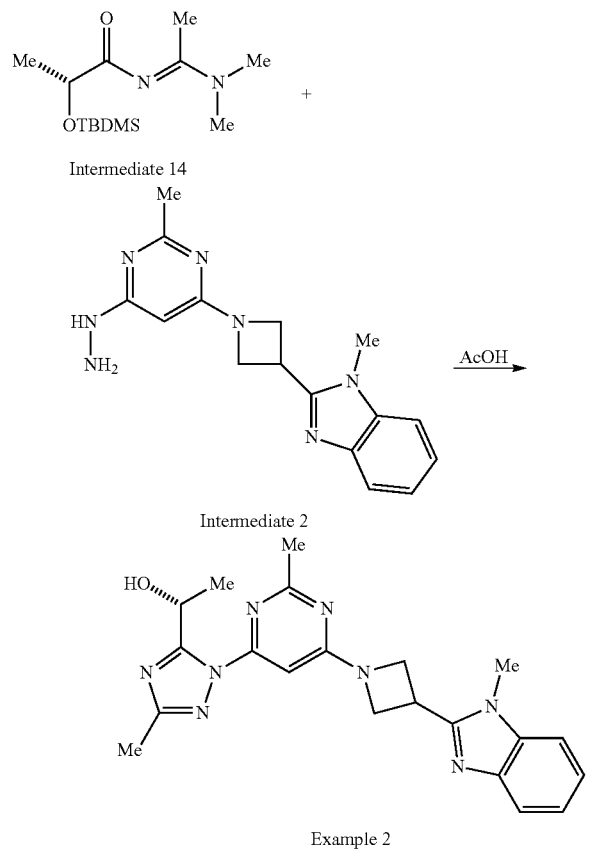

Example 2

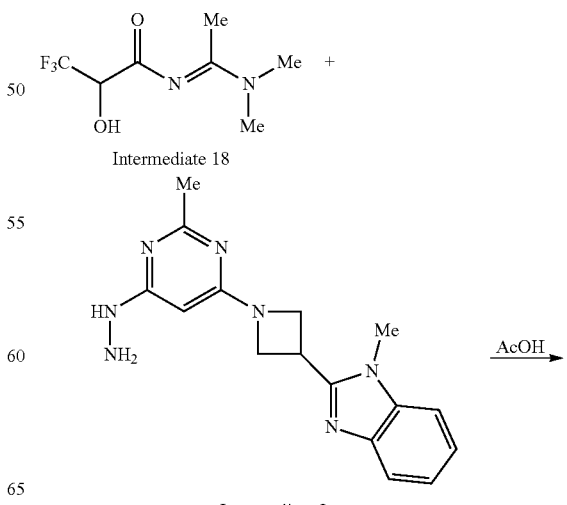

Intermediate 2

-continued

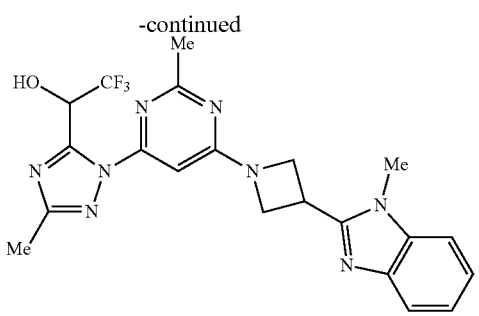

Example 3 chiral separation

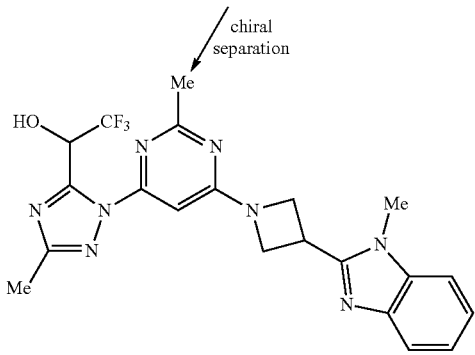

Example 3a
1st eluting

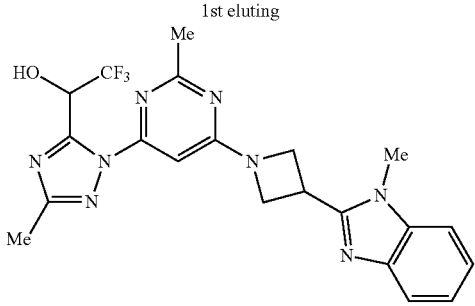

Example 3b
2nd eluting 2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol (Example 3)

To a solution of Intermediate 2 (5.5 g, 17.8 mmol) in AcOH (60 mL) was added the DME solution of Intermediate 18 (7.5 g, 35.6 mmol) and the reaction was heated at 80° C. for 1 h. Sampling of the reaction by LCMS suggested cyclization to the triazole had occurred with concomitant desilylation of the hydroxy group. The reaction was cooled to room temperature and brought to pH~8 by the slow addition of saturated aqueous sodium bicarbonate. The aqueous phase was extracted with EtOAc and the organic layer was dried over sodium sulfate, filtered, and concentrated. The crude product was purified by silica gel chromatography (0-10% 2-propanol/DCM) to give racemic Example 3. MS: m/z=459.3 (M+H).

The racemic mixture was separated by preparative chiral SFC on a Chiraltech ID column (2 cm id×25 cm length) eluting with 65% carbon dioxide/35% 2-propanol with 0.1% diethylamine modifier in isocratic mode at 50 mL/min.

Example 3a (1$^{st}$ eluting): $^1$H NMR (500 MHz, CDCl$_3$) δ 9.34-9.26 (m, 1H), 7.77-7.75 (m, 1H), 7.34-7.28 (m, 3H), 6.63 (s, 1H), 5.54-5.50 (m, 1H), 4.75-4.58 (br s, 4H), 4.33-4.30 (m, 1H), 3.75 (s, 3H), 2.53 (s, 3H), 2.46 (s, 3H); MS: m/z=459.5 (M+H).

Example 3b (2nd eluting): $^1$H NMR (500 MHz, CDCl$_3$) δ 9.33-9.31 (m, 1H), 7.77-7.75 (m, 1H), 7.35-7.28 (m, 3H), 6.63 (s, 1H), 5.56-5.51 (m, 1H), 4.76-4.56 (br s, 4H), 4.33-4.30 (m, 1H), 3.75 (s, 3H), 2.53 (s, 3H), 2.46 (s, 3H); MS: m/z=459.5 (M+H).

The following Examples were prepared in a similar manner by substituting the appropriate starting materials. Racemic compounds were separated by chiral SFC in a manner similar to Example 3 to provide enantiomers that are designated as 'first eluting' or 'second eluting'.

| Example | Structure | Name | MS m/z (M + H) |
| --- | --- | --- | --- |
| 4 | 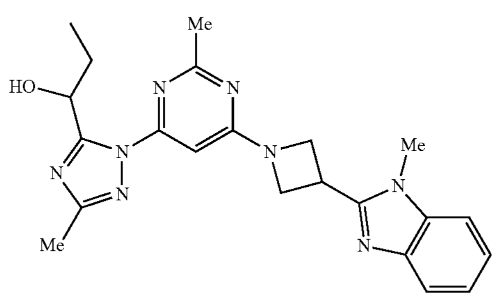 [SMILES: CCC(O)c1nc(C)nn1-c1cc(N2CC(c3nc4ccccc4n3C)C2)nc(C)n1] | 1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol | 419.5 |

| Example | Structure | Name | MS m/z (M + H) |
|---|---|---|---|
| 4a | 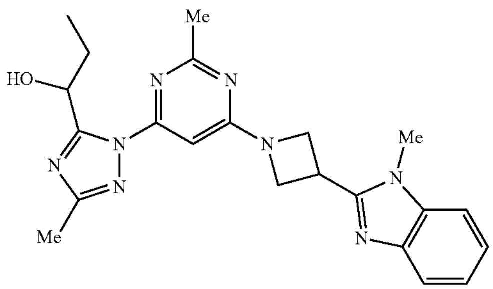 [SMILES: CCC(O)c1nc(C)nn1-c1cc(N2CC(c3nc4ccccc4n3C)C2)nc(C)n1] | 1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 1st eluting | 419.3 |
| 4b | 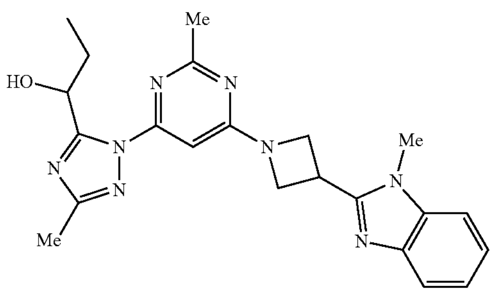 [SMILES: CCC(O)c1nc(C)nn1-c1cc(N2CC(c3nc4ccccc4n3C)C2)nc(C)n1] | 1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 2nd eluting | 419.3 |
| 5 | 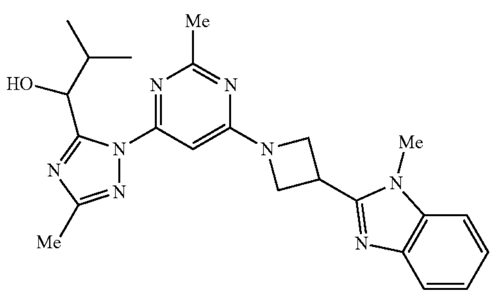 [SMILES: Cc1nc(N2CC(c3nc4ccccc4n3C)C2)cc(-n2nc(C)nc2C(O)C(C)C)n1] | 2-methyl-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol | 433.5 |
| 5a | 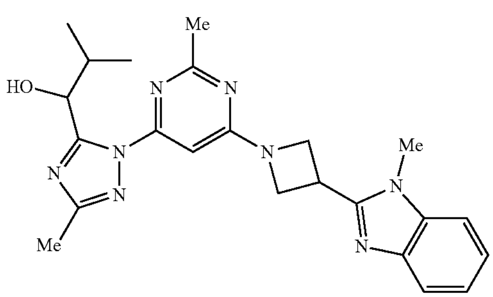 [SMILES: Cc1nc(N2CC(c3nc4ccccc4n3C)C2)cc(-n2nc(C)nc2C(O)C(C)C)n1] | 2-methyl-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 1st eluting | 433.5 |
| 5b | 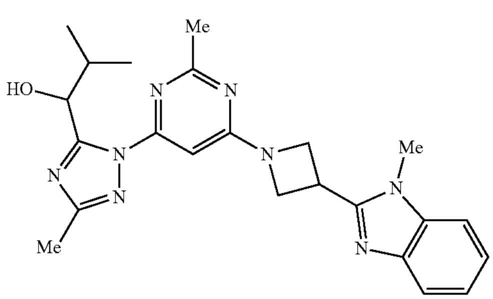 [SMILES: Cc1nc(N2CC(c3nc4ccccc4n3C)C2)cc(-n2nc(C)nc2C(O)C(C)C)n1] | 2-methyl-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 2nd eluting | 433.5 |

-continued

| Example | Structure | Name | MS m/z (M + H) |
|---|---|---|---|
| 6 | 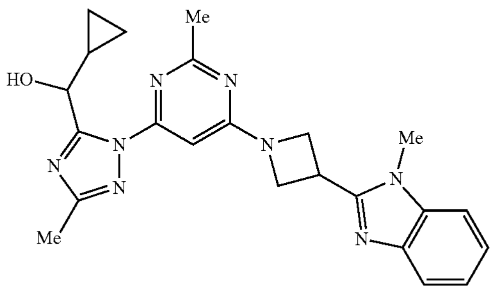 [SMILES: Cc1nc(N2CC(c3nc4ccccc4n3C)C2)cc(-n2nc(C)nc2C(O)C2CC2)n1] | cyclopropyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol | 431.5 |
| 6a | 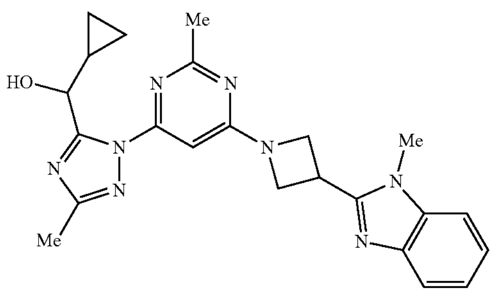 [SMILES: Cc1nc(N2CC(c3nc4ccccc4n3C)C2)cc(-n2nc(C)nc2C(O)C2CC2)n1] | cyclopropyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol - 1$^{st}$ eluting | 431.5 |
| 6b | 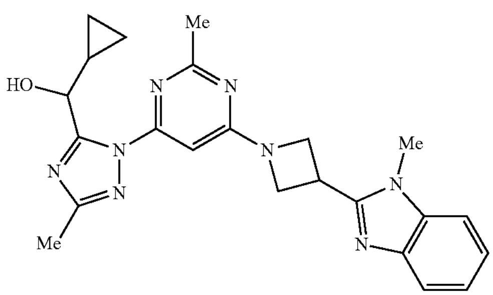 [SMILES: Cc1nc(N2CC(c3nc4ccccc4n3C)C2)cc(-n2nc(C)nc2C(O)C2CC2)n1] | cyclopropyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol - 2$^{nd}$ eluting | 431.5 |
| 7 | 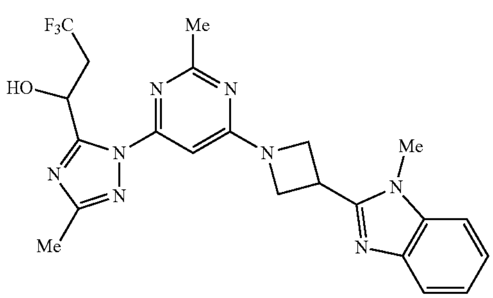 [SMILES: Cc1nc(N2CC(c3nc4ccccc4n3C)C2)cc(-n2nc(C)nc2C(O)CC(F)(F)F)n1] | 3,3,3-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol | 473.3 |
| 7a | 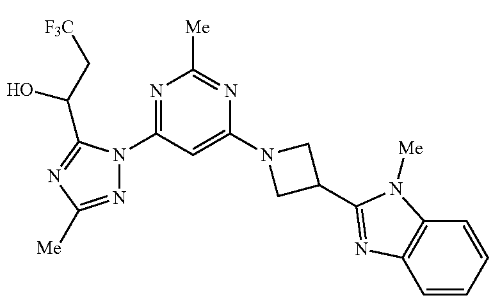 | 3,3,3-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 1$^{st}$ eluting | 473.3 |

| Example | Structure | Name | MS m/z (M + H) |
|---|---|---|---|
| 7b | 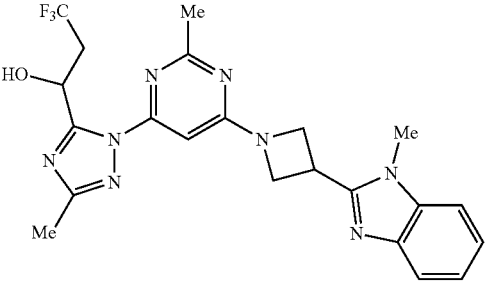 | 3,3,3-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol - 2nd eluting | 473.3 |
| 8 | 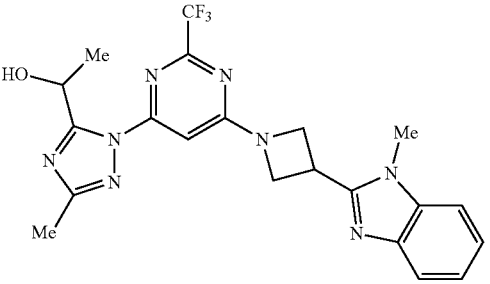 [SMILES: Cc1nc(C(C)O)n(-c2cc(N3CC(c4nc5ccccc5n4C)C3)nc(C(F)(F)F)n2)n1] | 1-(3-methyl-1-(6-(3-(1-methyl-1H-benzo[d]imidazol-2-yl)azetidin-1-yl)-2-(trifluoromethyl)pyrimidin-4-yl)-1H-1,2,4-triazol-5-yl)ethanol | 459.5 |
| 8a | 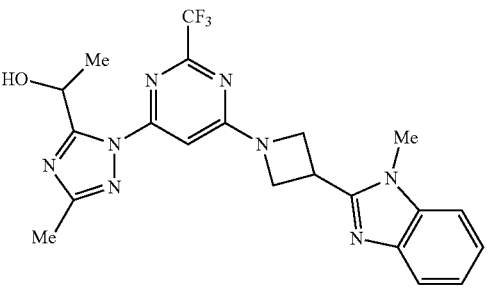 [SMILES: Cc1nc(C(C)O)n(-c2cc(N3CC(c4nc5ccccc5n4C)C3)nc(C(F)(F)F)n2)n1] | 1-(3-methyl-1-(6-(3-(1-methyl-1H-benzo[d]imidazol-2-yl)azetidin-1-yl)-2-(trifluoromethyl)pyrimidin-4-yl)-1H-1,2,4-triazol-5-yl)ethanol - 1st eluting | 459.4 |
| 8b | 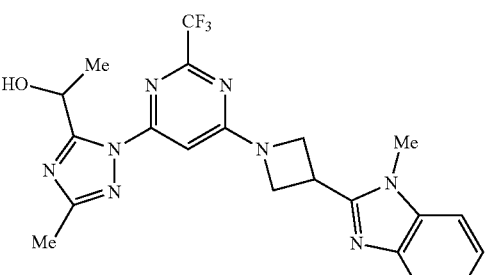 | 1-(3-methyl-1-(6-(3-(1-methyl-1H-benzo[d]imidazol-2-yl)azetidin-1-yl)-2-(trifluoromethyl)pyrimidin-4-yl)-1H-1,2,4-triazol-5-yl)ethanol - 2nd eluting | 459.5 |
| 9 | 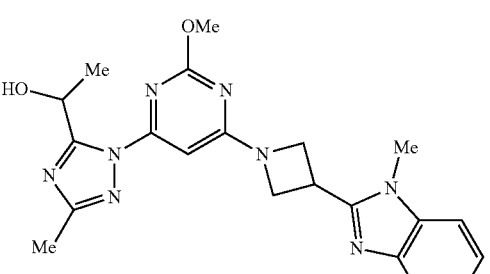 | 1-(1-(2-methoxy-6-(3-(1-methyl-1H-benzo[d]imidazol-2-yl)azetidin-1-yl)pyrimidin-4-yl)-3-methyl-1H-1,2,4-triazol-5-yl)ethanol | 421.5 |

-continued

| Example | Structure | Name | MS m/z (M + H) |
|---|---|---|---|
| 10 | 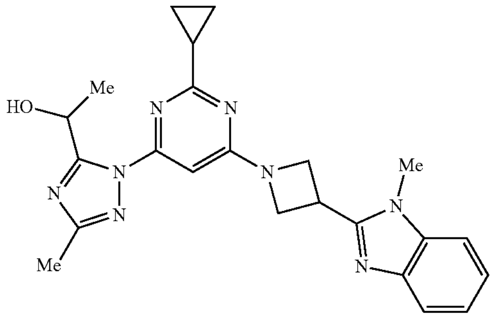 [SMILES: Cc1nc(C(C)O)n(-c2cc(N3CC(c4nc5ccccc5n4C)C3)nc(C3CC3)n2)n1] | 1-(1-(2-cyclopropyl-6-(3-(1-methyl-1H-benzo[d]imidazol-2-yl)azetidin-1-yl)pyrimidin-4-yl)-3-methyl-1H-1,2,4-triazol-5-yl)ethanol | 431.5 |
| 10a | 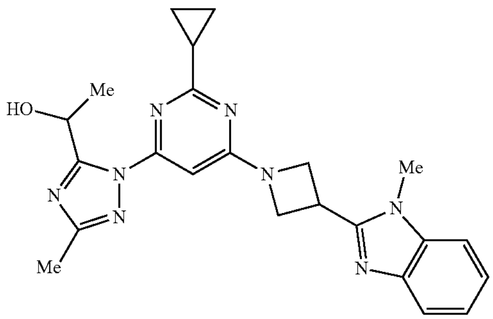 [SMILES: Cc1nc(C(C)O)n(-c2cc(N3CC(c4nc5ccccc5n4C)C3)nc(C3CC3)n2)n1] | 1-(1-(2-cyclopropyl-6-(3-(1-methyl-1H-benzo[d]imidazol-2-yl)azetidin-1-yl)pyrimidin-4-yl)-3-methyl-1H-1,2,4-triazol-5-yl)ethanol - 1st eluting | 431.5 |
| 10b | 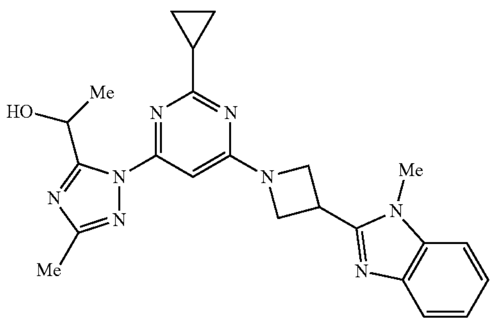 [SMILES: Cc1nc(C(C)O)n(-c2cc(N3CC(c4nc5ccccc5n4C)C3)nc(C3CC3)n2)n1] | 1-(1-(2-cyclopropyl-6-(3-(1-methyl-1H-benzo[d]imidazol-2-yl)azetidin-1-yl)pyrimidin-4-yl)-3-methyl-1H-1,2,4-triazol-5-yl)ethanol - 2nd eluting | 431.5 |
| 11a | 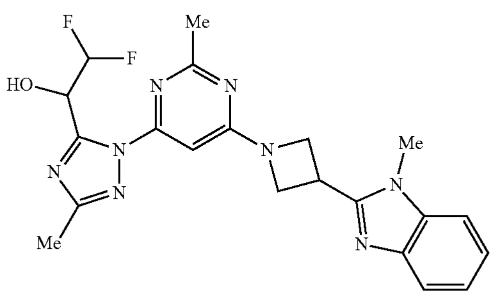 | 2,2-difluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol - 1st eluting | 441.3 |
| 11b | 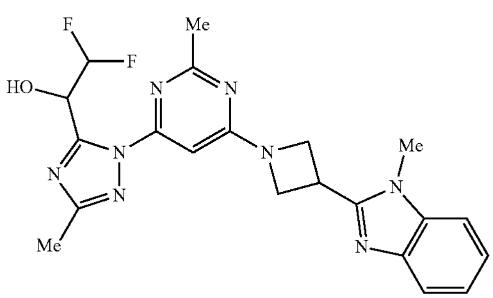 | 2,2-difluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol - 2nd eluting | 441.4 |

| Example | Structure | Name | MS m/z (M + H) |
|---|---|---|---|
| 12 | 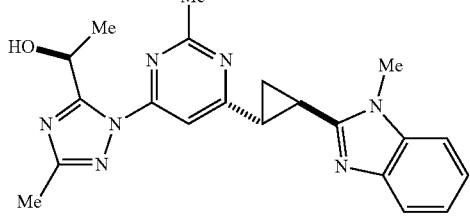 | 2-fluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol | 423.3 |

Example 13

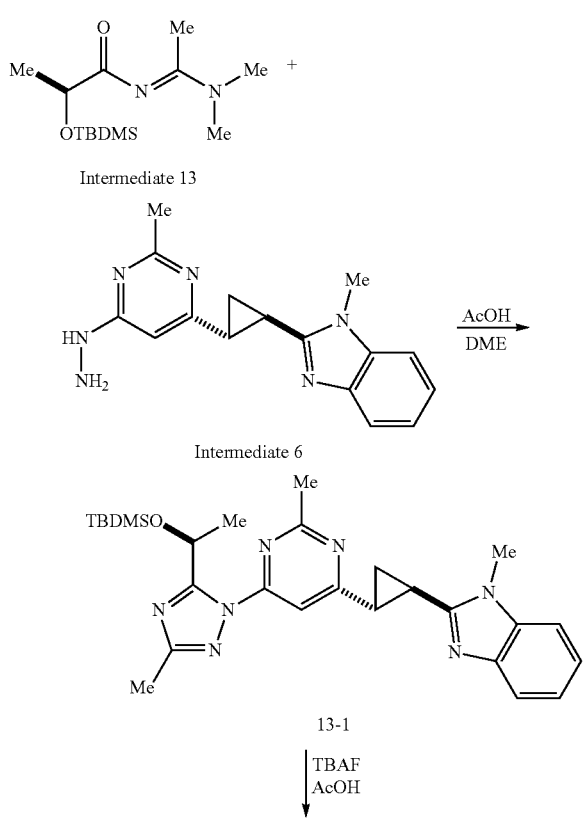

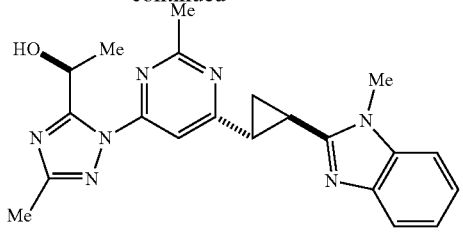

Example 13

Step 1:

2-((1R,2R)-2-(6-(5-((S)-1-((tert-butyldimethylsilyl)oxy)ethyl)-3-methyl-1H-1,2,4-triazol-1-yl)-2-methylpyrimidin-4-yl)cyclopropyl)-1-methyl-1H-benzo[d]imidazole (13-1)

To a solution of Intermediate 6 (1.8 g, 6.1 mmol) in acetic acid (40 ml) was added Intermediate 13 (4.0 g, 14.7 mmol) as a crude reaction mixture in 1,2-dimethoxyethane (40 mL). The reaction mixture was allowed to stir for 5 minutes at room temperature and then heated at 80° C. for 1 h. The reaction was cooled to room temperature, poured carefully over saturated aqueous sodium bicarbonate solution (200 mL), and the aqueous layer was made basic to pH~8 by the addition of solid sodium bicarbonate. The solution was extracted with ethyl acetate (200 mL) and the organic layer was dried over sodium sulfate, filtered and concentrated. The crude product was purified by silica gel chromatography (0-60% EtOAc/hexanes) to afford 13-1 as an oil. MS: m/z=504.4 (M+H).

Step 2:

(S)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol (Example 13)

A solution of 13-1 (2.8 g, 5.6 mmol), acetic acid (0.41 ml, 7.2 mmol) and 1 N tetrabutylammonium fluoride (7.8 mL, 7.8 mmol) in THF (15.6 ml) was stirred at 23° C. for 16 h. Additional 1 N tetrabutylammonium fluoride in THF (4 mL, 4 mmol) was added and stirring was continued for 16 h. The white precipitate that formed was collected by filtration, washed with THF (2×50 mL) followed by ether (2×50 mL). The white solid was dissolved in DCM (100 mL) and washed with saturated aqueous sodium bicarbonate solution (2×100 mL), brine (2×100 mL) and water (2×100 mL) successively. The organic layer was dried over sodium sulfate, filtered, and concentrated to afford a clear oil. The oil was triturated from 5:1 ether/EtOAc and the resulting white solid was collected by filtration and air dried to provide Example 13. $^1$H NMR (500 MHz, CDCl$_3$) δ 7.77 (s, 1H), 7.71-7.69 (m, 1H), 7.32-7.24 (m, 3H), 6.12 (d, 1H, J=5.4 Hz), 5.19-5.17 (m, 1H), 3.83 (s, 3H), 2.89-2.86 (m, 2H), 2.73 (s, 3H), 2.44 (s, 3H), 2.09-2.00 (m, 2H), 1.73 (d, 3H, J=6.6 Hz); MS: m/z=390.3 (M+H).

The following Examples were prepared in a similar manner by substituting the appropriate starting materials:

| Example | Structure | Name | MS m/z (M + H) |
|---|---|---|---|
| 14 | 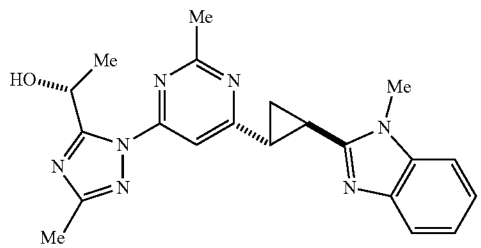 | (R)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol | 390.3 |
| 15 | 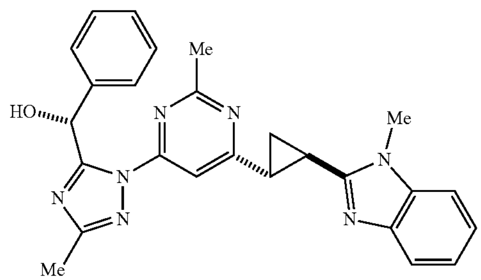 | (R)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol | 452.5 |
| 16 | 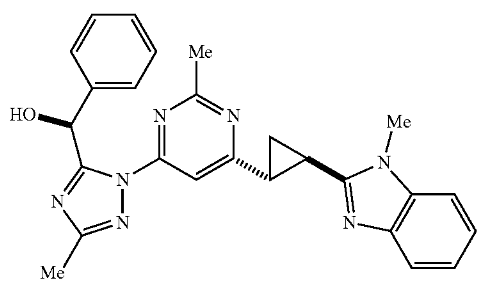 | (S)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol | 452.5 |
| 17 | 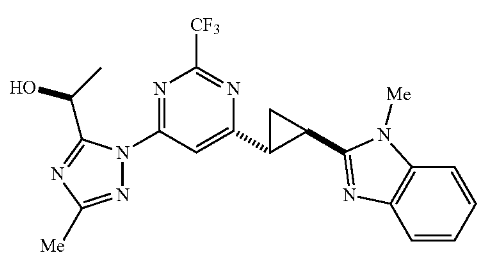 | (S)-1-(3-methyl-1-(6-((1R,2R)-2-(1-methyl-1H-benzo[d]imidazol-2-yl)cyclopropyl)-2-(trifluoromethyl)pyrimidin-4-yl)-1H-1,2,4-triazol-5-yl)ethanol | 444.2 |
| 18 | 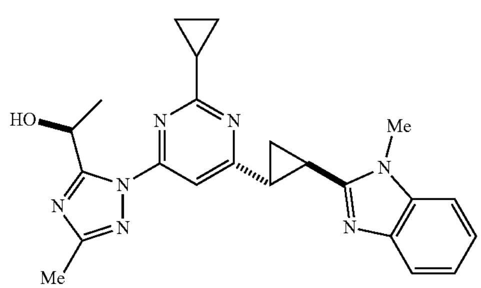 | (S)-1-(1-(2-cyclopropyl-6-((1R,2R)-2-(1-methyl-1H-benzo[d]imidazol-2-yl)cyclopropyl)pyrimidin-4-yl)-3-methyl-1H-1,2,4-triazol-5-yl)ethanol | 416.3 |

Example 19

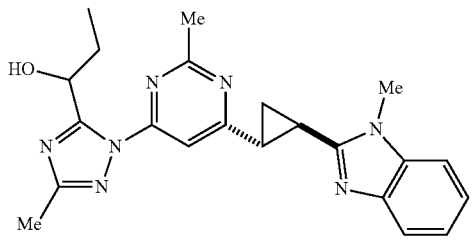

Scheme:

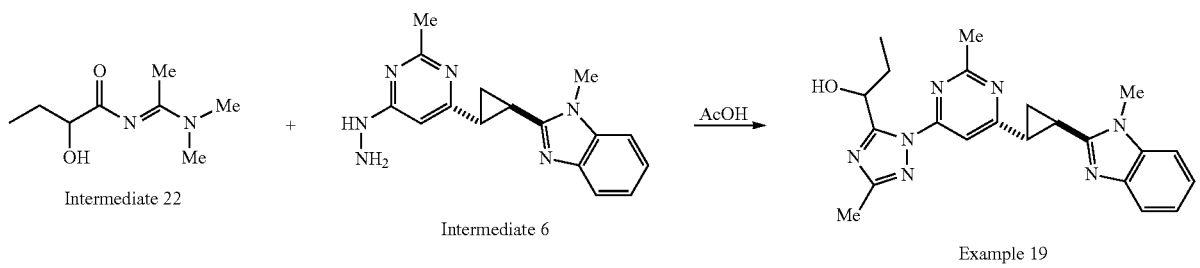

Example 19 as a mixture of diastereomers at the secondary alcohol carbon. $^1$H NMR (500 MHz, CDCl$_3$) δ 7.76 (s, 1H), 7.71-7.69 (m, 1H), 7.31-7.25 (m, 3H), 5.96-5.89 (m, 1H), 4.99-4.95 (m, 1H), 3.84 (s, 3H), 2.89-2.86 (m, 2H) 2.73 (s, 3H), 2.43 (s, 3H), 2.11-1.99 (m, 4H), 1.10-1.03 (m, 3H); MS: m/z=404.5 (M+H).

The mixture of diastereomers was separated by preparative chiral SFC on a ChiralPak AD-H column (3 cm id×25 cm length) eluting with 80% carbon dioxide/20% MeOH with 0.1% diethylamine modifier in isocratic mode at 80 mL/min.

Example 19a (1$^{st}$ eluting): $^1$H NMR (500 MHz, CDCl$_3$) δ 7.76 (s, 1H), 7.71-7.69 (m, 1H), 7.31-7.25 (m, 3H), 5.95 (d, J=7.0 Hz, 1H), 4.99-4.95 (m, 1H), 3.84 (s, 3H), 2.89-2.86

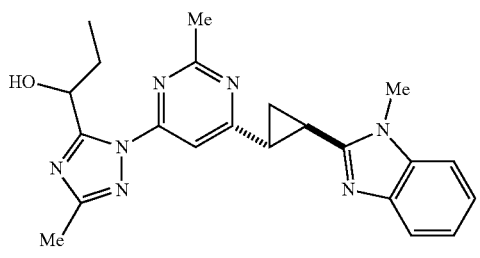

Example 19a
1st eluting

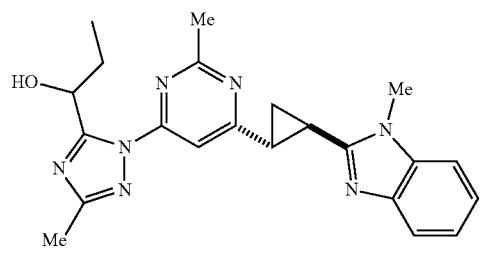

Example 19b
2nd eluting 1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol (Example 19)

To a mixture of Intermediate 6 (50 mg, 0.17 mmol) in AcOH (3 mL) was added the DME solution of Intermediate 22 (116 mg, 0.55 mmol) in one portion. The reaction was heated at 80° C. for 30 min and then cooled to room temperature. The mixture was partitioned between saturated aqueous sodium bicarbonate and EtOAc and the aqueous layer was adjust to pH~8. The organic layer was dried over sodium sulfate, filtered, and concentrated. The crude product was purified by reverse-phase HPLC (5-95% ACN/water containing 0.1% NH$_4$OH, Phenomenex Axia) to afford (m, 2H) 2.73 (s, 3H), 2.43 (s, 3H), 2.11-1.99 (m, 4H), 1.10-1.03 (m, 3H); MS: m/z=404.5 (M+H).

Example 19b (2nd eluting): $^1$H NMR (500 MHz, CDCl$_3$) δ 7.76 (s, 1H), 7.71-7.69 (m, 1H), 7.31-7.25 (m, 3H), 5.89 (d, J=6.6 Hz, 1H), 4.99-4.95 (m, 1H), 3.83 (s, 3H), 2.89-2.86 (m, 2H) 2.73 (s, 3H), 2.43 (s, 3H), 2.11-1.99 (m, 4H), 1.10-1.03 (m, 3H); MS: m/z=404.5 (M+H).

The following Examples were prepared in a similar manner by substituting the appropriate starting materials. When applicable, diastereomeric compound mixtures were separated by chiral SFC in a manner similar to Example 19 to provide diastereomers that are designated as 'first eluting' or 'second eluting'.

| Example | Structure | Name | MS m/z (M + H) |
|---|---|---|---|
| 20 | 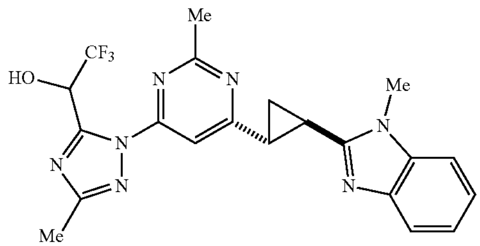 | 2,2,2-trifluoro-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol | 444.4 |
| 20a | 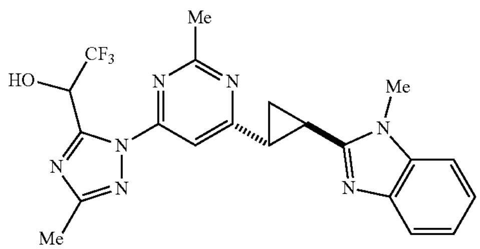 | 2,2,2-trifluoro-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol - 1$^{st}$ eluting | 444.4 |
| 20b | 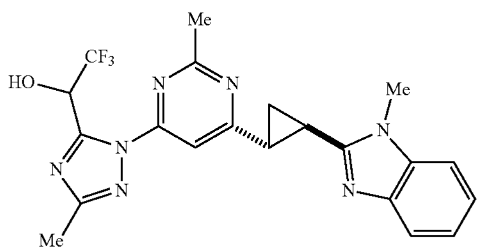 | 2,2,2-trifluoro-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol - 2$^{nd}$ eluting | 444.4 |
| 21 | 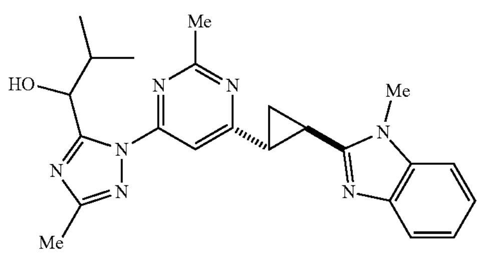 | 2-methyl-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol | 418.5 |

The following table shows representative data for the compounds of the Examples as PDE10 inhibitors as determined by the foregoing assays. In this table, the PDE10 Ki is a measure of the ability of the test compound to inhibit the action of the PDE10 enzyme.

| Example | PDE10a Ki (nM) |
|---|---|
| 1 | 0.23 |
| 2 | 1.2 |
| 3 | 0.11 |
| 3a | 1.0 |
| 3b | 0.06 |
| 4 | 0.51 |
| 4a | 1.8 |
| 4b | 0.41 |
| 5 | 0.41 |
| 5a | 0.34 |
| 5b | 0.77 |
| 6 | 0.36 |
| 6a | 0.17 |
| 6b | 2.6 |
| 7 | 3.2 |
| 7a | 4.5 |
| 7b | 2.5 |
| 8 | 0.83 |
| 8a | 0.53 |
| 8b | 1.0 |
| 9 | 1.2 |
| 10 | 0.21 |
| 10a | 0.13 |
| 10b | 0.39 |
| 11a | 0.65 |
| 11b | 3.0 |
| 12 | 0.34 |
| 13 | 0.74 |
| 14 | 1.1 |
| 15 | 0.09 |
| 16 | 0.62 |
| 17 | 2.8 |
| 18 | 0.36 |
| 19 | 1.3 |
| 19a | 0.55 |
| 19b | 0.59 |
| 20 | 0.55 |
| 20a | 0.58 |

-continued

| Example | PDE10a Ki (nM) |
|---|---|
| 20b | 0.92 |
| 21 | 0.47 |

With respect to other substituted triazolyl compounds such as those disclosed in U.S. Ser. No. 61/544,055, the present compounds exhibit unexpected properties, such as improved potency against the PDE10 enzyme and reduced potential for drug-drug interactions based on CYP inhibition. This includes reversible inhibition of CYP2C9 and time-dependent inhibition (TDI) of CYP3A4.

For example, the following compounds are disclosed in U.S. Ser. No. 61/544,055:

2-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-2-ol (Compound A)

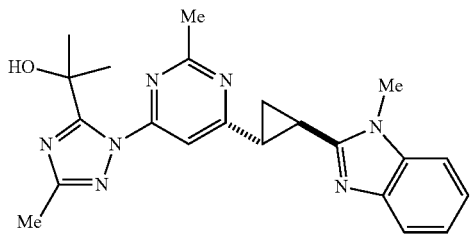

2-((1R,2R)-2-(6-(5-((S)-1-methoxyethyl)-3-methyl-1H-1,2,4-triazol-1-yl)-2-methylpyrimidin-4-yl)cyclopropyl)-1-methyl-1H-benzo[d]imidazole (Compound B)

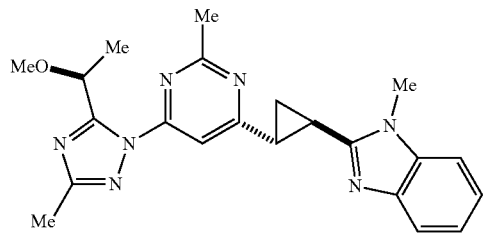

2-((1R,2R)-2-(6-(5-(methoxymethyl)-3-methyl-1H-1,2,4-triazol-1-yl)-2-methylpyrimidin-4-yl)cyclopropyl)-1-methyl-1H-benzo[d]imidazole (Compound C)

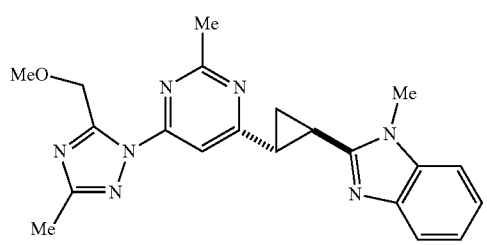

Representative compounds herein are listed in the following Table and their properties with respect to PDE10 potency, CYP3A4 TDI, and CYP2C9 inhibition are compared to those of Compounds A, B, and C.

| Compound/Example | PDE10 Ki (nM) | TDI CYP3A4 shift ratio | CYP2C9 $IC_{50}$ (uM) |
|---|---|---|---|
| A | 4.2 | 1 | >50 |
| B | 2.1 | 1 | 10.5 |
| C | 0.49 | >1.98 | 46 |
| 1 | 0.23 | 1 | >50 |
| 2 | 1.2 | 1 | >50 |
| 3b | 0.06 | 1 | >50 |
| 4b | 0.51 | 1 | >50 |
| 6a | 0.17 | 1 | >50 |
| 13 | 0.74 | 1 | >50 |
| 14 | 1.1 | 1 | >50 |
| 19a | 0.55 | 1 | >50 |

As noted by this data, the compounds of the present invention as illustrated by Examples 1, 2, 3b, 4b, 6a, 13, 14, and 19a display increased potency against the PDE10 enzyme compared to Compounds A and B. This may translate into improved in vivo efficacy and the potential for a lower dose.

Further, Compound B inhibits the CYP2C9 enzyme with an $IC_{50}$ of 10.5 uM while Examples 1, 2, 3b, 4b, 6a, 13, 14, and 19a all have $IC_{50}$ values of >50 uM for inhibition of CYP2C9 and suggests that compounds of the present invention may have reduced risk for a CYP2C9 mediated drug-drug interaction as compared to Compound B.

Compound C has comparable potency against the PDE10 enzyme (Ki=0.49 nM) to many compounds of the present invention. However, this compound exhibited time-dependent inhibition (TDI) of the CYP3A4 enzyme which is a development risk due to the potential for a drug-drug interaction in humans (for a leading reference, see: Obach R S, Walsky R L, and Venkatakrishnan K (2007) Mechanism-based inactivation of human cytochrome P450 enzymes and the prediction of drug-drug interactions. *Drug Metab Dispos* 35:246-255). Examples 1, 2, 3b, 4b, 6a, 13, 14, and 19a do not exhibit TDI of CYP3A4, suggesting a benefit for compounds of this type.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

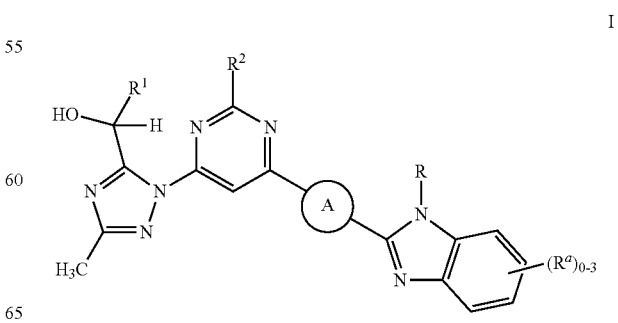

wherein:

A represents

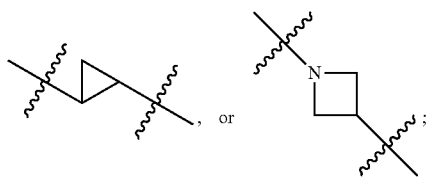 [SMILES: *C1CC1* ; *C1CN(*)C1], or ;

R represents H or $C_{1-6}$alkyl;
$R^1$ is selected from the groups consisting of $(CH_2)_nC_{1-4}$ haloalkyl, $C_{1-6}$alkyl, $C_{3-6}$cycloalkyl, $C_{6-10}$aryl, said alkyl cycloalkyl, and aryl is unsubstituted or substituted with 1 to 3 groups of $R^a$;
$R^2$ is selected from the group consisting of H, O—R, CN, $O(CH_2)_nOR$, $OCHR(CH_2)_nOR$, SR, $SO_2R$, $S(O)R$, $N(R)_2$, $C(O)N(R)_2$, $C_{1-3}$ haloalkyl, $O(CH_2)_nC_{1-3}$haloalkyl, $O(CH_2)_n$ $C_{3-6}$cycloalkyl, $(CH_2)_nC_{5-10}$ heterocycle, $C_{1-6}$ alkyl, and $C_{3-10}$cycloalkyl, said alkyl, cycloalkyl, and heterocycle is unsubstituted or substituted with 1 to 3 groups of $R^a$;
$R^a$ is selected from the group consisting of:
(1) halogen,
(2) hydroxyl,
(3) $C_{1-6}$alkyl,
(4) —$(CH_2)_nO$—R,
(5) $(CH_2)_n$ $C_{6-10}$aryl,
(6) $(CH_2)_nC_{5-10}$ heterocycle,
(7) $OC_{1-5}$ haloalkyl;
(8) $CO_2R$;
(9) $C(O)N(R)_2$;
(10) $(CH_2)_nC(O)R$;
(11) CN,
(12) $(CH_2)_nN(R)_2$;
(13) $(CH_2)_nC_{3-6}$cycloalkyl,
(14) $(CH_2)_nC_{1-3}$ haloalkyl;
n represents 0-4,
or a pharmaceutically acceptable salt thereof.

2. The compound according to claim 1 wherein A is

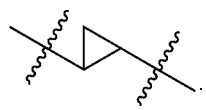 [SMILES: *C1CC1*].

3. The compound according to claim 1 wherein A is

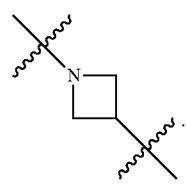 [SMILES: *C1CN(*)C1].

4. The compound according to claim 1 wherein $R^1$ is $C_{1-6}$ alkyl.

5. The compound according to claim 1 wherein $R^1$ is $(CH_2)_nC_{1-4}$ haloalkyl.

6. The compound according to claim 1 wherein $R^1$ is optionally substituted $C_{6-10}$ aryl.

7. The compound according to claim 1 wherein $R^1$ is $C_{3-6}$ cycloalkyl.

8. The compound according to claim 1 represented by structural formula Ia:

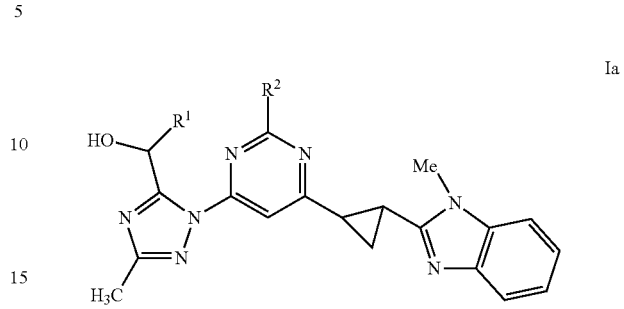

or a pharmaceutically acceptable salt thereof, wherein $R^1$ is C1-6 alkyl, $CF_3$, C6-10 aryl, or C3-6 cycloalkyl.

9. The compound according to claim 8 wherein $R^1$ is methyl, ethyl, propyl, $CF_3$, phenyl, or cyclohexyl and $R^2$ is methyl, ethyl, propyl, $CF_3$, or cyclopropyl.

10. The compound according to claim 1 represented by structural formula Iaa:

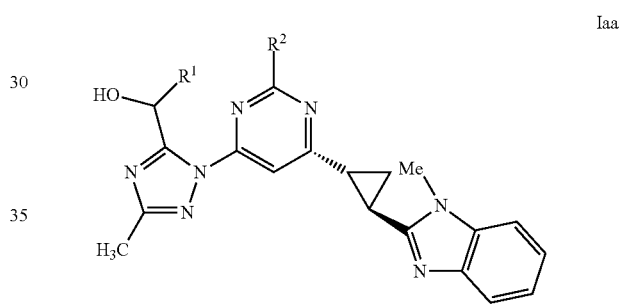

or a pharmaceutically acceptable salt thereof, wherein $R^1$ is C1-6 alkyl, $CF_3$, C6-10 aryl, or C3-6 cycloalkyl.

11. The compound according to claim 10 wherein $R^1$ is methyl, ethyl, propyl, $CF_3$, phenyl, or cyclohexyl and $R^2$ is methyl, ethyl, propyl, $CF_3$, or cyclopropyl.

12. The compound according to claim 1 represented by structural formula Ib:

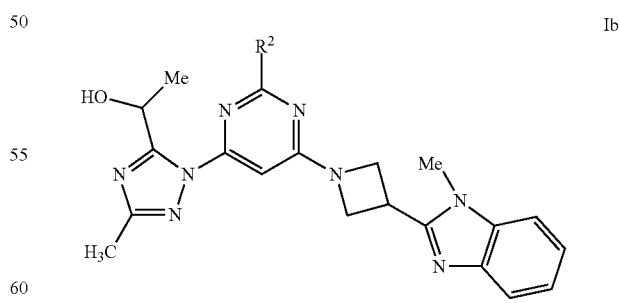

or a pharmaceutically acceptable salt thereof wherein $R^1$ is C1-6 alkyl, $CF_3$, C6-10 aryl, or C3-6 cycloalkyl.

13. The compound according to claim 12 wherein $R^1$ is methyl, ethyl, propyl, $CF_3$, phenyl, or cyclohexyl and $R^2$ is methyl, ethyl, propyl, $CF_3$, or cyclopropyl.

14. A compound which is:

1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

(S)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

(R)-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl) ethanol;

1-(3-methyl-1-(6-(3-(1-methyl-1H-benzo[d]imidazol-2-yl)azetidin-1-yl)-2-(trifluoromethyl)pyrimidin-4-yl)-1H-1,2,4-triazol-5-yl)ethanol;

1-(1-(2-methoxy-6-(3-(1-methyl-1H-benzo[d]imidazol-2-yl)azetidin-1-yl)pyrimidin-4-yl)-3-methyl-1H-1,2,4-triazol-5-yl)ethanol;

1-(1-(2-cyclopropyl-6-(3-(1-methyl-1H-benzo[d]imidazol-2-yl)azetidin-1-yl)pyrimidin-4-yl)-3-methyl-1H-1,2,4-triazol-5-yl)ethanol;

2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

(S)-2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

(R)-2,2,2-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

2,2-difluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

2-fluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)ethanol;

(S)-cyclohexyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;

(R)-cyclohexyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;

(S)-(3-methyl-1-(2-methyl-6-(3-(1-methyl-1H-benzo[d]imidazol-2-yl)azetidin-1-yl)pyrimidin-4-yl)-1H-1,2,4-triazol-5-yl)(phenyl)methanol;

(R)-(3-methyl-1-(2-methyl-6-(3-(1-methyl-1H-benzo[d]imidazol-2-yl)azetidin-1-yl)pyrimidin-4-yl)-1H-1,2,4-triazol-5-yl)(phenyl)methanol;

1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;

2-methyl-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;

cyclopropyl(3-methyl-1-(2-methyl-6-(3-(1-methyl-1H-benzo[d]imidazol-2-yl)azetidin-1-yl)pyrimidin-4-yl)-1H-1,2,4-triazol-5-yl)methanol;

3,3,3-trifluoro-1-(3-methyl-1-(2-methyl-6-(3-(1-methyl-1H-benzo[d]imidazol-2-yl)azetidin-1-yl)pyrimidin-4-yl)-1H-1,2,4-triazol-5-yl)propan-1-ol;

1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;

(R)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;

(S)-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;

(R)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol;

(S)-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)(phenyl)methanol;

2,2,2-trifluoro-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)ethanol;

1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol;

2-methyl-1-(3-methyl-1-(2-methyl-6-((1R,2R)-2-(1-methyl-1H-benzo[d]imidazol-2-yl)cyclopropyl)pyrimidin-4-yl)-1H-1,2,4-triazol-5-yl)propan-1-ol;

1-(3-methyl-1-(6-((1R,2R)-2-(1-methyl-1H-benzo[d]imidazol-2-yl)cyclopropyl)-2-(trifluoromethyl)pyrimidin-4-yl)-1H-1,2,4-triazol-5-yl)ethanol;

(S)-1-(3-methyl-1-(6-((1R,2R)-2-(1-methyl-1H-benzo[d]imidazol-2-yl)cyclopropyl)-2-(trifluoromethyl)pyrimidin-4-yl)-1H-1,2,4-triazol-5-yl)ethanol;

1-(1-(2-cyclopropyl-6-((1R,2R)-2-(1-methyl-1H-benzo[d]imidazol-2-yl)cyclopropyl)pyrimidin-4-yl)-3-methyl-1H-1,2,4-triazol-5-yl)ethanol (S)-1-(1-(2-cyclopropyl-6-((1R,2R)-2-(1-methyl-1H-benzo[d]imidazol-2-yl)cyclopropyl)pyrimidin-4-yl)-3-methyl-1H-1,2,4-triazol-5-yl)ethanol;

or a pharmaceutically acceptable salt thereof.

15. A pharmaceutical composition which comprises a pharmaceutically acceptable carrier and a compound of claim 1 or a pharmaceutically acceptable salt thereof.

16. A method for treating anxiety in a mammalian patient in need thereof which comprises administering to the patient a therapeutically effective amount of a compound of claim 1 or a pharmaceutically acceptable salt thereof.

* * * * *